United States Patent
Serhan

(10) Patent No.: US 6,433,202 B1
(45) Date of Patent: Aug. 13, 2002

(54) PREVENTION OF NEUTROPHIL RECRUITMENT

(75) Inventor: Charles N. Serhan, Wellesley, MA (US)

(73) Assignee: Brigham and Women's Hospital, Boston, MA (US)

( * ) Notice: Subject to any disclaimer, the term of this patent is extended or adjusted under 35 U.S.C. 154(b) by 0 days.

(21) Appl. No.: 09/525,742

(22) Filed: Mar. 14, 2000

Related U.S. Application Data

(60) Provisional application No. 60/125,209, filed on Mar. 18, 1999.

(51) Int. Cl.[7] .............................................. C07C 59/00
(52) U.S. Cl. ........................ 554/213; 554/219; 558/303; 568/21; 568/22; 568/28
(58) Field of Search ................................ 554/213, 219; 558/303; 568/21, 22, 28

(56) References Cited

U.S. PATENT DOCUMENTS 5,441,951 A    8/1995    Serhan ........................ 514/213

FOREIGN PATENT DOCUMENTS

WO    WO 98/11049    3/1998

OTHER PUBLICATIONS

Weissmann, G. (1991) *Sci. Am.* 264, 84–90.
Ridker, P. M., Cushman, M., Stampfer, M. J., Tracy, R. P. & Hennekens, C. H. (1997) *N. Engl. J. Med.* 336, 973–979.
Marcus, A. J. (1995) *N. Engl. J. Med.* 333, 656–658.
Herschman, H.R. (1998) *Trends Cardiovasc. Med.* 8, 145–150.
Serhan, C. N. (1997) *Prostaglandins* 53, 107–137.
Chiang, N., Takano, T., Clish, C. B., Petasis, N. A., Tai, H.–H. & Serhan, C. N. (1998) *J. Pharmacol. Exp. Ther.* 287, 779–790.
Lee, T. H., Crea, A. E., Gant, V., Spur, B. W., Marron, B. E., Nicolaou, K. C., Reardon, E., Brezinski, M. & Serhan, C. N. (1990) *Am. Rev. Respir. Dis.* 141, 1453–1458.
Chavis, C., Chanez, P., Vachier, I., Bousquet, J., Michel, F. B. & Godard, P. (1995) *Biochem. Biophys. Res. Commun.* 207, 273–279.
Chavis, C., Vachier, I., Chanez, P., Bousquet, J. & Godard, P. (1996) *J. Exp. Med.* 183, 1633–1643.
Thomas, E., Leroux, J. L., Blotman, F. & Chavis, C. (1995) *Inflamm. Res.* 44, 121–124.
Gewirtz, A. T., McCormick, B., Neish, A. S., Petasis, N. A., Gronert, K., Serhan, C. N. & Madara, J. L. (1998) *J. Clin. Invest.* 101, 1860–1869.
Pillinger, M. H. & Abramson, S. B. (1995) *Rheum. Dis. Clin North Am.* 21, 691–714.
Hagihara, H., Nomoto, A., Mutoh, S., Yamaguchi, I. & Ono, T. (1991) *Atherosclerosis* 91, 107–116.
McLaughlan, J. M., Seth, R., Vautier, G., Robins, R. A., Scott, B. B., Hawkey, C. J. & Jenkins, D. (1997) *J. Pathol.* 181, 87–92.
Anezaki, K., Asakura, H., Honma, T., Ishizuka, K., Funakoshi, K., Tsukada, Y. & Narisawa, R. (1998) *Intern. Med.* 37, 253–258.
Iverson, L. & Kragballe, K. (1997) in *Skin Immune System (SIS)*, ed. Bos, J. D. (CRC Press, Boca Raton), pp. 227–237.
Ensor, C. M. & Tai, H.–H. (1991) in *Prostaglandins, Leukotrienes, Lipoxins, and PAF*, ed. Bailey, J. M. (Plenum Press, New York), pp. 39–52.

(List continued on next page.)

Primary Examiner—Deborah D. Carr
(74) Attorney, Agent, or Firm—Dorsey & Whitney LLC; Scott D. Rothenberger

(57) ABSTRACT

Aspirin (ASA) triggers a switch in the biosynthesis of lipid mediators, inhibiting prostanoid production and initiating 15-epi-lipoxin generation, through the acetylation of cyclooxygenase II.

6 Claims, 9 Drawing Sheets

OTHER PUBLICATIONS

Serhan, C. N., Fiore, S., Brezinski, D. A. & Lynch, S. (1993) *Biochemistry* 32, 6313–6319.

Maddox, J. F., Colgan, S. P., Clish, C. B., Petasis, N. A., Fokin, V. V. & Serhan, C. N. (1998) *FASEB J.* 12, 487–494.

Serhan, C. N., Maddox, J. F., Petasis, N. A., Akritopoulou–Zanze, I., Papayianni, A., Brady, H. R., Colgan, S. P. & Madara, J. L. (1995) *Biochemistry* 34, 14609–14615.

Takano, T., Clish, C. B., Gronert, K., Petasis, N. & Serhan, C. N. (1998) *J. Clin. Invest.* 101, 819–826.

Sin, Y. M., Sedgwick, A. D., Chea, E. P. & Willoughby, D. A. (1986) *Ann. Rheum. Dis.* 45, 873–877.

Bradley, P. P., Priebat, D. A., Christensen, R. D. & Rothstein, G. (1982) *J. Invest. Dermatol.* 78, 206–209.

Edwards, J. C. W., Sedgwick, A. D. & Willoughby, D. A. (1981) *J. Pathol.* 134, 147–156.

Tessier, P. A., Naccache, P. H., Clark–Lewis, I., Gladue, R. P., Neote, K. S. & McColl, S. R. (1997) *J. Immunol.* 159, 3595–3602.

Dahlén, S. E. & Serhan, C. N. (1991) in *Lipoxygenases and Thier Products*, eds. Crookes, S. T. & Wong, A. (Academic Press, San Diego, CA), pp. 235–276.

Katoh, T., Takahashi, K., DeBoer, D. K., Serhan, C. N. & Badr, K. F. (1992) *Am. J. Physiol.* 263, F436–442.

Marriott, J. B., Westby, M. & Dalgleish, A. G. (1997) *Drug Discovery Today* 2, 273–282.

International Search Report, Jul. 10, 2000.

Abstract No. 252676t "Neutrophil–Mediated Changes in Vascular Permeability are Inhibited by Topical Application of Aspirin–Triggered 15–epi–Lipoxin $A_4$ and Novel Lipoxin $B_4$ Stable Analogs" *Chemical Abstracts*, vol. 128, No. 21, p. 41, Col. R, (1998).

PREVENTION OF NEUTROPHIL RECRUITMENT

CROSS-REFERENCE TO RELATED APPLICATIONS

This application claims priority to U.S. Provisional Patent Application No. 60/125,209 filed Mar. 18, 1999, the contents of which are incorporated herein by reference.

STATEMENT REGARDING FEDERALLY SPONSORED RESEARCH

The work leading to this invention was supported by grants GM-38765 and DK-5 0305 for the National Institute of Health. The U.S. Government therefore may have certain rights in this invention.

BACKGROUND OF THE INVENTION

Aspirin (acetylsalicylic acid, ASA) has been available for use as an analgesic-antipyretic for almost a century and novel therapeutic applications for this drug, for example in lowering the risk of myocardial infarction or as a prophylaxis against colorectal cancer, continue to be uncovered (Weissmann, G. (1991) *Sci. Am.* 264, 84–90; Ridker, P. M., Cushman, M., Stampfer, M. J., Tracy, R. P. & Hennekens, C. H. (1997) *N. Engl. J. Med.* 336, 973–979; Marcus, A. J. (1995) *N. Engl. J. Med.* 333, 656–658). The acetylation of cyclooxygenases I and II (COX I and II) and the subsequent irreversible inhibition of prostaglandin (PG) and thromboxane biosyntheses are well understood mechanisms of some of ASA's pharmacological actions (Marcus, A. J. (1995) *N. Engl. J. Med.* 333, 656–658; Herschman, H. R. (1998) *Trends Cardiovasc. Med.* 8, 145–150). More recently, ASA was found to cause a switch in eicosanoid biosynthesis as the acetylation of COX II changes the enzyme's activity to produce 15R-hydroxyeicosatetraenoic acid from agonist-released arachidonic acid Herschman, H. R. (1998) *Trends Cardiovasc. Med.* 8, 145–150). Human neutrophils, and other cells possessing 5-lipoxygenase, utilize this substrate via transcellular biosynthetic routes to produce 15-epi-lipoxin $A_4$ (15-epi-$LXA_4$) and 15-epi-lipoxin $B_4$ (15-epi-$LXB_4$) (Serhan, C. N. (1997) Prostaglandins 53, 107–137; Chiang, N., Takano, T., Clish, C. B., Petasis, N. A., Tai, H.-H. & Serhan, C. N. (1998) *J. Pharmacol. Exp. Ther.* 287, 779–790). These aspirin-triggered lipoxins (ATL) are the endogenous 15R enantiomeric counterparts of lipoxin $A_4$ ($LXA_4$) and lipoxin $B_4$ ($LXB_4$), respectively, and share their bioactivities (Serhan, C. N. (1997) *Prostaglandins* 53, 107–137(5)).

Unlike other eicosanoids (e.g., leukotrienes, PGs, etc.), which are generally considered local pro-inflammatory mediators, lipoxins (LX) display potent inhibitory actions in several key events in inflammation, such as polymorphonuclear cell (PMN) chemotaxis, transmigration across endothelial and epithelial cells, and diapedesis from post-capillary venules (Serhan, C. N. (1997) *Prostaglandins* 53, 107–137(5)). LX are generated in several pathogenic scenarios in vivo, for example: in lung tissue of patients with severe pulmonary disease; and by PMN from patients with asthma or rheumatoid arthritis, where their presence is proposed to be linked to long-term clinical improvement (Lee, T. H., Crea, A. E., Gant, V., Spur, B. W., Marron, B. E., Nicolaou, K. C., Reardon, E., Brezinski, M. & Serhan, C. N. (1990) *Am. Rev. Respir. Dis.* 141, 1453–1458; Chavis, C., Chanez, P., Vachier, I., Bousquet, J., Michel, F. B. & Godard, P. (1995) *Biochem. Biophys. Res. Commun.* 207, 273–279; Chavis, C., Vachier, I., Chanez, P., Bousquet, J. & Godard, P. (1996) *J. Exp. Med.* 183, 1633–1643; Thomas, E., Leroux, J. L., Blotman, F. & Chavis, C. (1995) *Inflamm. Res.* 44, 121–124). Interestingly, ATL show an even greater level of inhibition than native LX in preventing neutrophil adhesion, where they are ~twice as potent (Serhan, C. N. (1997) *Prostaglandins* 53, 107–137). ATL are also more potent inhibitors of microbial induction of cytokine release. Specifically, 15-epi-$LXA_4$ showed greater inhibition than $LXA_4$ of *S. typhimurium*-induced secretion and gene regulation of the potent leukocyte chemoattractant IL-8, generated by intestinal epithelial cells (Gewirtz, A. T., McCormick, B., Neish, A. S., Petasis, N. A., Gronert, K., Serhan, C. N. & Madara, J. L. (1998) *J. Clin. Invest.* 101, 1860–1869). It is therefore likely that, in addition to the inhibition of prostaglandin formation, the benefits of ASA therapy also result from the triggering of novel anti-inflammatory lipid mediators that act locally to down regulate leukocytes.

SUMMARY OF THE INVENTION

In one aspect, the present invention is directed to compounds having the formulae (I–V):

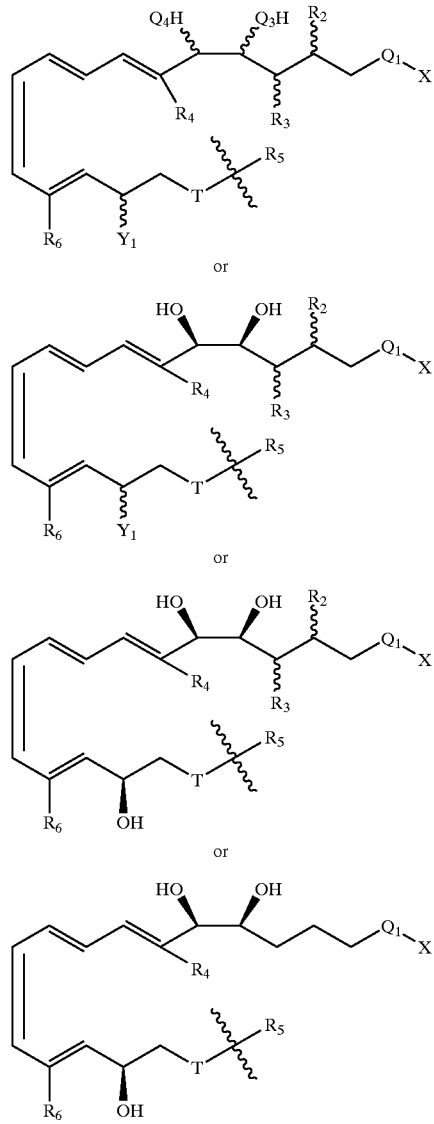

-continued or

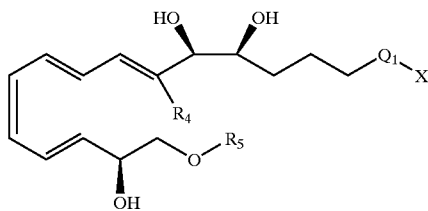

wherein X is $R_1$, $OR_1$, or $SR_1$;

wherein $R_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

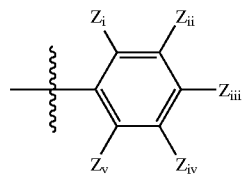

wherein $Z_i$, $Z_{ii}$, $Z_{iii}$, $Z_{iv}$ and $Z_v$ are each independently selected from $—NO_2$, $—CN$, $—C(=O)—R_1$, $—SO_3H$, a hydrogen atom, halogen, methyl, $—OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;

wherein $Q_1$ is (C=O), $SO_2$ or (CN), provided when $Q_1$ is CN, then X is absent;

wherein $Q_3$ and $Q_4$ are each independently O, S or NH;

wherein one of $R_2$ and $R_3$ is a hydrogen atom and the other is
(a) H;
(b) an alkyl of 1 to 8 carbon atoms, inclusive, which may be straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$, wherein $Q_2$ is $—O—$ or $—S—$; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is
(a) H;
(b) an alkyl of 1 to 6 carbon atoms, inclusive, which may be straight chain or branched;

wherein $R_5$ is

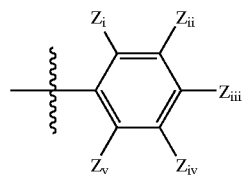

wherein $Z_i$, $Z_{ii}$, $Z_{iii}$, $Z_{iv}$ and $Z_v$ are each independently selected from $—NO_2$, $—CN$, $—C(=O)—R_1$, $—SO_3H$, a hydrogen atom, halogen, methyl, $—OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is $—OH$, methyl, $—SH$, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is
(a) H;
(b) an alkyl from 1 to 4 carbon atoms, inclusive, straight chain or branched;

wherein T is O or S, and pharmaceutically acceptable salts thereof excluding 16-phenoxy-$LXA_4$ and/or 15-epi-16-(para-fluoro)-phenoxy-$LXA_4$ in certain embodiments.

In preferred embodiments, X is $OR_1$ wherein $R_1$ is a hydrogen atom, an alkyl group of 1 to 4 carbon atoms or a pharmaceutically acceptable salt, $Q_1$ is C=O, $R_2$ and $R_3$, if present, are hydrogen atoms, $R_4$ is a hydrogen atom or methyl, $Q_3$ and $Q_4$, if present, are both O, $R_6$, if present, is a hydrogen atom, $Y_1$, if present, is OH, T is O and $R_5$ is a substituted phenyl, e.g.,

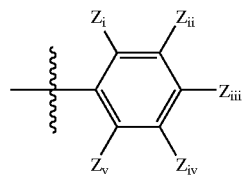

wherein $Z_i$, $Z_{ii}$, $Z_{iii}$, $Z_{iv}$ and $Z_v$ are each independently selected from $—NO_2$, $—CN$, $—C(=O)—R_1$, $—SO_3H$, a hydrogen atom, halogen, methyl, $—OR_x$, wherein $R_x$ is 1 to 8 carbon atoms, inclusive, which may be a straight chain or branched, and hydroxyl. In certain embodiments for $R_5$, 15-epi-16-para-fluorophenyl, 15-epi-unsubstituted phenyl, 16-parafluorophenyl or 16-phenyoxy are excluded.

In another aspect, the present invention is directed to an in vivo method for modulating a disease or condition associated with polymorphoneutrophil (PMN) inflammation. The method includes administering to a subject an effective anti-inflammatory amount of a pharmaceutical composition including a compound having one of the above-described formulae.

In another aspect, the invention is directed to a method for modulating a disease or condition associated with polymorphoneutrophil (PMN) inflammation. The method includes administering to a subject an effective anti-inflammatory amount of a pharmaceutical composition including a compound having one of the above-described formulae.

In still another aspect, the present invention is directed to pharmaceutical compositions including compounds having the above-described formulae and a pharmaceutically acceptable carrier. In one embodiment, a preferred compound is

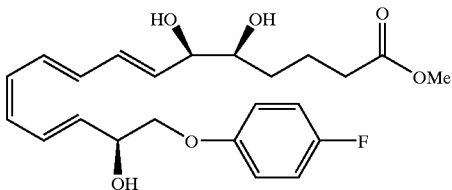

In a preferred embodiment, the pharmaceutical carrier is not a ketone, e.g., acetone.

In yet another aspect, the present invention is directed to a packaged pharmaceutical composition for treating a PMN responsive state in a subject. The packaged pharmaceutical composition includes a container holding a therapeutically effective amount of at least one lipoxin compound having one of the formulae described above and instructions for using the lipoxin compound for treating an PMN responsive state in the subject.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
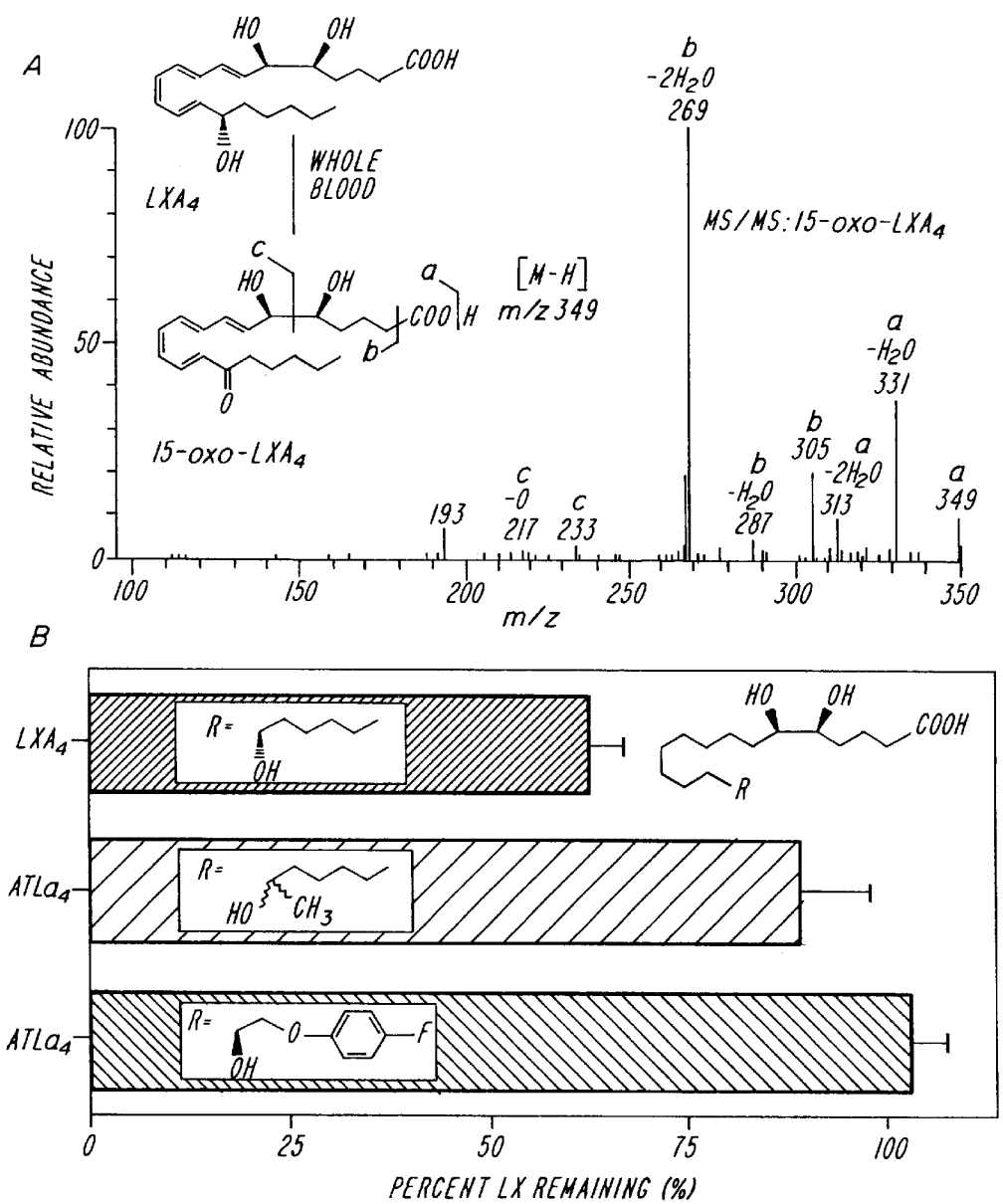
FIG. 1 depicts (A) Initial metabolic step of $LXA_4$ inactivation in mouse whole blood and 15-oxo-$LXA_4$ MS/MS spectrum. $LXA_4$ (21 μM) was incubated ex vivo in mouse whole blood for 3 h. The MS/MS spectrum of the major oxo-product is indicative of 15-oxo-$LXA_4$, with diagnostic product ions at m/z: 349 (a=[M–H]$^-$), 331 (a-$H_2O$), 313 (a-$2H_2O$), 305 (b=[M–H]$^-$–$CO_2$), 287 (b-$H_2O$), 269 (b-$2H_2O$), 233 (c), and 217 (c–O). (B) Biostability of $LXA_4$ and stable analogs in mouse whole blood. $LXA_4$, 15(R/S)-methyl-$LXA_4$ ($ATLa_1$, which carries a racemic methyl group at C-15), and 15-epi-16-(para-fluoro)-phenoxy-$LXA_4$ ($ATLa_2$, in which a bulky (para-fluoro)-phenoxy group replaces the ω-chain at C-16) were added (see Methods) to heparinized mouse whole blood and incubated at 37 °C. for 0 and 3 h. Following centrifugation at 800×g and 0° C., the plasma supernatants were drawn off and stopped in two volumes of ice cold methanol. The lipoxins were extracted by solid phase methodology and quantitated by LC/MS/MS. Values represent means±SEM (n=3–4).

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Aspirin (ASA) triggers a switch in the biosynthesis of lipid mediators, inhibiting prostanoid production and initiating 15-epi-lipoxin generation, through the acetylation of cyclooxygenase II. These aspirin-triggered lipoxins (ATL) may mediate some of ASA's beneficial actions and therefore are of interest in the search for novel anti-inflammatories that could manifest fewer unwanted side-effects. Design modifications to native ATL structure prolong its biostability in vivo. In mouse whole blood, ATL analogs protected at carbon 15 (ATLa$_1$) and the omega end (ATLa$_2$) were recoverable to ~90 and 100% at 3 hours, respectively, compared to a ~40% loss of native lipoxin A$_4$ (LXA$_4$). ATLa$_2$ retains bioactivity and, at levels as low as ~24 nmol/mouse, potently inhibited TNF-α-induced leukocyte recruitment into the dorsal air pouch. Inhibition was evident by either local intra-air pouch delivery (~77% inhibition) or via systemic delivery by intravenous injection (~85% inhibition) and proved more potent than local delivery of either ASA or dexamethasone. Rank order for inhibiting PMN infiltration was: ATLa$_2$ (10 μg, i.v.)≈ATLa$_2$ (10 μg, local)>ASA (1.0 mg, local)≈dexamethasone (10 μg, local). Applied topically to mouse ear skin, ATLa$_2$ also inhibited PMN infiltration induced by leukotriene B$_4$ (~78% inhibition) or phorbol ester, which initiates endogenous chemokine production (~49% inhibition). These results indicate that this fluorinated analog of natural aspirin-triggered LXA$_4$ is bioavailable by either local or systemic delivery routes and is a more potent and precise inhibitor of neutrophil accumulation than ASA.

Abbreviations: ASA, Aspirin, acetylsalicylic acid; ATL, aspirin-triggered lipoxins; ATLa$_1$, 15(R/S)-methyl-lipoxin A$_4$; ATLa$_2$, 15-epi-16-(para-fluoro)-phenoxy-lipoxin A$_4$; COX I and II, cyclooxygenases I and II; 15-epi-LXA$_4$, 15-epi-lipoxin A$_4$, 5S,6R,15R-trihydroxyeicosa-7E,9E,11Z,13E-tetraenoic acid; 15-epi-LXB$_4$, 15-epi-lipoxin B$_4$, 5S,14R,15R-trihydroxyeicosa-6E,8Z,10E,12E-tetraenoic acid; i.v., intravenous; LC/MS/MS, liquid chromatography-tandem mass spectrometry; LTB$_4$, leukotriene B$_4$, 5S,12R-dihydroxyeicosa-6E,8Z,10Z,14E-eicosatetraenoic acid; LX, lipoxins; LXA$_4$, lipoxin A$_{4,}$ $_5$S,6R,15S-trihydroxyeicosa-7E, 9E,11Z,13E-tetraenoic acid; LXB$_4$, lipoxin B$_4$, 5S,14R,15S-trihydroxyeicosa-6E,8Z,10E,12E-tetraenoic acid; PG, prostaglandin; PMA, phorbol 12-myristate 13-acetate; PMN, polymorphonuclear leukocyte; TNF-α, tumor necrosis factor α.

PMN accumulation and activation play central roles in the pathogenesis of a wide range of disease states as diverse as rheumatoid arthritis, atherosclerosis, ulcerative colitis, and psoriasis (Pillinger, M. H. & Abramson, S. B. (1995) *Rheum. Dis. Clin. North Am.* 21, 691–714; Hagihara, H., Nomoto, A., Mutoh, S., Yamaguchi, I. & Ono, T. (1991) *Atherosclerosis* 91, 107–116; McLaughlan, J. M., Seth, R., Vautier, G., Robins, R. A., Scott, B. B., Hawkey, C. J. & Jenkins, D. (1997) *J. Pathol.* 181, 87–92; Anezaki, K., Asakura, H., Honma, T., Ishizuka, K., Funakoshi, K., Tsukada, Y. & Narisawa, R. (1998) *Intern. Med.* 37, 253–258; Iverson, L. & Kragballe, K. (1997) in *Skin Immune System* (SIS), ed. Bos, J. D. (CRC Press, Boca Raton), pp. 227–237). Hence the elucidation of endogenous regulatory mechanisms that can control neutrophil functions are of considerable therapeutic interest. Because they are small lipophilic compounds amenable to total organic synthesis, the natural lipoxins, and specifically their endogenous isoform ATL, are well suited as potential leads for novel small molecule therapeutics as well as pharmacologic tools for uncovering endogenous counter-regulatory and/or anti-inflammatory signaling pathways.

Design modifications that enhance biostability are advantageous since the lipoxins are autacoids that are rapidly biosynthesized in response to stimuli, in turn elicit counter-regulatory responses, and then are rapidly enzymatically inactivated (Serhan, C. N. (1997) *Prostaglandins* 53, 107–137). 15-Hydroxy-prostaglandin dehydrogenase (15-PGDH), which catalyzes the reversible oxidation of the carbon-15 position alcohol group of prostaglandins and several other ω-6-hydroxylated fatty acids, also catalyzes the first step of lipoxin inactivation (FIG. 1A) (Ensor, C. M. & Tai, H.-H. (1991) in *Prostaglandins, Leukotrienes, Lipoxins, and PAF*, ed. Bailey, J. M. (Plenum Press, New York), pp. 39–52; Serhan, C. N., Fiore, S., Brezinski, D. A. & Lynch, S. (1993) *Biochemistry* 32, 6313–6319; Maddox, J. F., Colgan, S. P., Clish, C. B., Petasis, N. A., Fokin, V. V. & Serhan, C. N. (1998) *FASEB J.* 12, 487–494). In view of these findings, several stable analogs of ATL and LXA$_4$ were designed that resist oxidation at carbon-15 by recombinant dehydrogenase in vitro (Serhan, C. N., Maddox, J. F., Petasis, N. A., Akritopoulou-Zanze, I., Papayianni, A., Brady, H. R., Colgan, S. P. & Madara, J. L. (1995) *Biochemistry* 34, 14609–14615). These LX act at LXA$_4$ receptors on leukocytes and are active within the nanomolar range: inhibiting PMN adherence, transmigration, and diapedesis (Takano, T., Clish, C. B., Gronert, K., Petasis, N. & Serhan, C. N. (1998) *J. Clin. Invest.* 101, 819–826). Design modifications to native ATL biostabilize these mediators in whole blood to resist rapid inactivation. Moreover, the fluorinated ATL analog, namely 15-epi-16-(para-fluoro)-phenoxy-LXA$_4$ (ATLa$_2$), is a potent inhibitor of PMN recruitment in murine in vivo models when administered through both local and systemic routes.

The present invention is directed to new lipoxin compounds. In one embodiment, the compound has the formula (I)

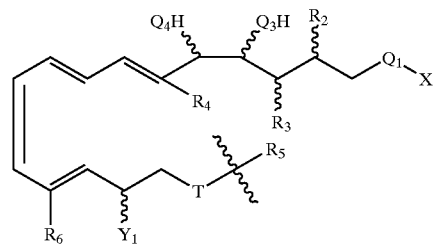

wherein X is R$_1$, OR$_1$, or SR$_1$;
wherein R$_1$ is
  (i) a hydrogen atom;
  (ii) an alkyl of 1 to 8 carbons atoms, inclusive, which may be straight chain or branched;
  (iii) a cycloalkyl of 3 to 10 carbon atoms;
  (iv) an aralkyl of 7 to 12 carbon atoms;
  (v) phenyl;
  (vi) substituted phenyl

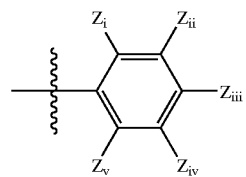

wherein $Z_i$, $Z_{ii}$, $Z_{iii}$, $Z_{iv}$ and $Z_v$ are each independently selected from —NO$_2$, —CN, —C(=O)—

$R_1$, —SO$_3$H, a hydrogen atom, halogen, methyl, —OR$_x$, wherein R$_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;

wherein $Q_1$ is (C=O), SO$_2$ or (CN), provided when $Q_1$ is CN, then X is absent;

wherein $Q_3$ and $Q_4$ are each independently O, S or NH;

wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$ wherein $Q_2$ is —O— or —S—; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is
(a) H;
(b) an alkyl of 1 to 6 carbon atoms, inclusive, which may be a straight chain or branched;

wherein $R_5$ is

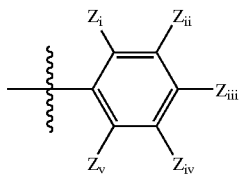

wherein $Z_i$, $Z_{ii}$, $Z_{iii}$, $Z_{iv}$ and $Z_v$ are each independently selected from —NO$_2$, —CN, —C(=O)—R$_1$, —SO$_3$H, a hydrogen atom, halogen, methyl, —OR$_x$, wherein R$_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or CH$_a$Z$_b$ where a+b=3, a=0 to 3, b=0 to 3 and Z is cyano, nitro or a halogen;

wherein $R_6$ is
(a) H;
(b) an alkyl from 1 to 4 carbon atoms, inclusive, straight chain or branched;

wherein T is O or S, and pharmaceutically acceptable salts thereof, excluding 16-phenoxy-LXA$_4$ and 15-epi-16-(para-fluoro)-phenoxy-LXA$_4$.

In another embodiment, compounds useful in the invention have the formula (II)

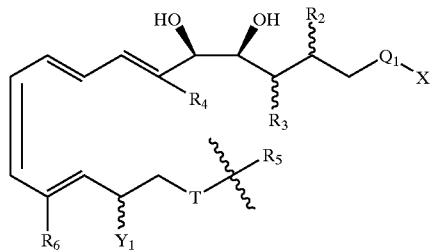

wherein X is $R_1$, OR$_1$, or SR$_1$; wherein R$_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

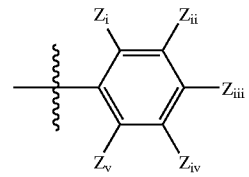

wherein $Z_i$, $Z_{ii}$, $Z_{iii}$, $Z_{iv}$ and $Z_v$ are each independently selected from —NO$_2$, —CN, —C(=O)—R$_1$, —SO$_3$H, a hydrogen atom, halogen, methyl, —OR$_x$, wherein R$_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;

wherein $Q_1$ is (C=O), SO$_2$ or (CN), provided when $Q_1$ is CN, then X is absent;

wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$ wherein $Q_2$ is —O— or —S—; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is
(a) H;
(b) an alkyl of 1 to 6 carbon atoms, inclusive, which may be a straight chain or branched;

wherein $R_5$ is

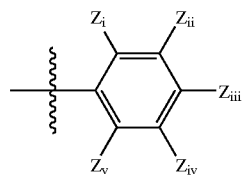

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_1$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is
(a) H;
(b) an alkyl from 1 to 4 carbon atoms, inclusive, straight chain or branched;

wherein T is O or S, and pharmaceutically acceptable salts thereof, excluding 16-phenoxy-$LXA_4$ and 15-epi-16-(para-fluoro)-phenoxy-$LXA_4$.

The invention is also directed to useful lipoxin compounds having the formula (III)

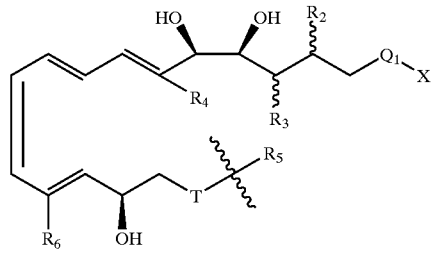

wherein X is $R_1$, $OR_1$, or $SR_1$;
wherein $R_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

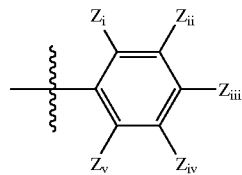

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;

(vii) a detectable label molecule; or
(viii) a straight or branched chain alkenyl of 2 to 8 carbon atoms, inclusive;

wherein $Q_1$ is (C=O), $SO_2$ or (CN), provided when $Q_1$ is CN, then X is absent;

wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$ wherein $Q_2$ is —O— or —S—; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is
(a) H;
(b) an alkyl of 1 to 6 carbon atoms, inclusive, which may be a straight chain or branched;

wherein $R_5$ is

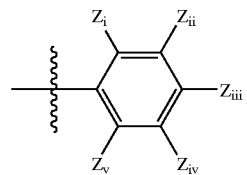

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_1$ wherein $R_x$ is 1 to 8 carbon atoms, inclusive, which may be a straight chain or branched, and hydroxyl or a substituted or unsubstituted, branched or unbranched alkyl group;

wherein $R_6$ is
(a) H;
(b) an alkyl from 1 to 4 carbon atoms, inclusive, straight chain or branched;

wherein T is O or S, and pharmaceutically acceptable salts thereof, excluding 16-phenoxy-$LXA_4$ and 15-epi-16-(para-fluoro)-phenoxy-$LXA_4$.

The invention is further directed to useful lipoxin compounds having the formula (IV)

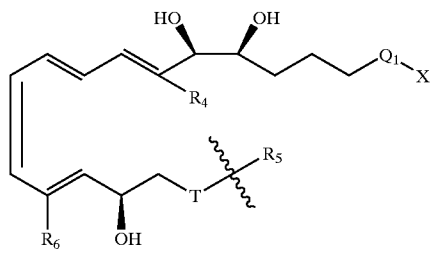

wherein X is $R_1$, $OR_1$, or $SR_1$;
wherein $R_1$ is
(i) a hydrogen atom;
(ii) an alkyl of 1 to 8 carbons atoms, inclusive, which may be straight chain or branched;

(iii) a cycloalkyl of 3 to 10 carbon atoms;
(iv) an aralkyl of 7 to 12 carbon atoms;
(v) phenyl;
(vi) substituted phenyl

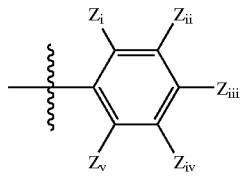

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $R_4$ is
(a) H;
(b) an alkyl of 1 to 6 carbon atoms, inclusive, which may be a straight chain or branched;
wherein $R_5$ is

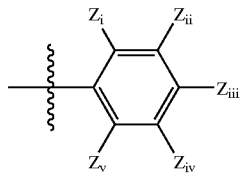

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;
wherein $R_6$ is
(a) H;
(b) an alkyl from 1 to 4 carbon atoms, inclusive, straight chain or branched;
wherein T is O or S, and pharmaceutically acceptable salts thereof, excluding 16-phenoxy-$LXA_4$ and 15-epi-16-(para-fluoro)-phenoxy-$LXA_4$.

The invention is further directed to useful lipoxin compounds having the formula (V)

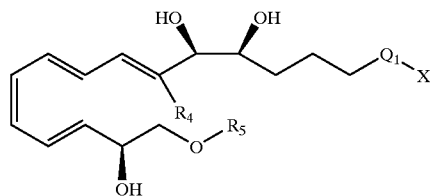

wherein X is $R_1$, $OR_1$, or $SR_1$;
wherein $R_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

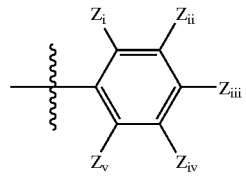

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $R_4$ is
(a) H;
(b) an alkyl of 1 to 6 carbon atoms, inclusive, which may be a straight chain or branched;
wherein $R_5$ is

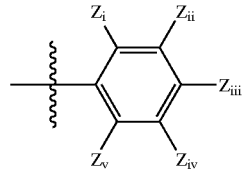

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;
wherein $R_6$ is
(a) H;
(b) an alkyl from 1 to 4 carbon atoms, inclusive, straight chain or branched; and
pharmaceutically acceptable salts thereof, excluding 16-phenoxy-$LXA_4$ and 15-epi-16-(para-fluoro)-phenoxy-$LXA_4$.

In preferred embodiments, X is $OR_1$ wherein $R_1$ is a hydrogen atom, an alkyl group of 1 to 4 carbon atoms or a pharmaceutically acceptable salt, $Q_1$ is C=O, $R_2$ and $R_3$, if present, are hydrogen atoms, $R_4$ is a hydrogen atom or methyl, $Q_3$ and $Q_4$, if present, are both O, $R_6$, if present, is a hydrogen atom, $Y_1$, if present, is OH, T is O and $R_5$ is a substituted phenyl, e.g.,

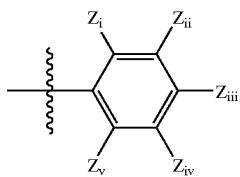

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group. In certain embodiments para-fluorophenyl and unsubstituted phenyl groups are excluded from $R_5$.

In another aspect, the present invention is directed to an in vivo method for modulating a disease or condition associated with polymorphoneutrophil (PMN) inflammation. The method includes administering to a subject an effective anti-inflammatory amount of a pharmaceutical composition including a compound having one of the above-described formulae.

In another aspect, the invention is directed to a method for modulating a disease or condition associated with polymorphoneutrophil (PMN) inflammation. The method includes administering to a subject an effective anti-inflammatory amount of a pharmaceutical composition including a compound having one of the above-described formulae.

In still another aspect, the present invention is directed to pharmaceutical compositions including compounds having the above-described formulae and a pharmaceutically acceptable carrier. In one embodiment, a preferred compound is

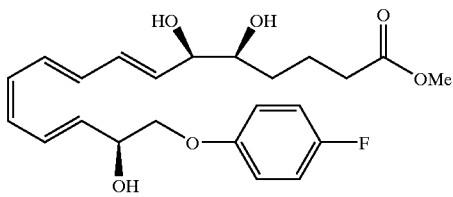

In a preferred embodiment, the pharmaceutical carrier is not a ketone, e.g., acetone.

In one embodiment, the antiinflammatories of the invention can be incorporated into a shampoo or a body cleansing product, e.g., a soap, for cleansing of the scalp and/or body. The use of these compounds in a shampoo or soap product can be used to treat psoriasis, seborrheic dermatitis, pustular dermatosis and dandruff. Thus the compounds are useful for modulating PMN inflammation associated with such conditions.

In yet another aspect, the present invention is directed to a packaged pharmaceutical composition for treating a PMN responsive state in a subject. The packaged pharmaceutical composition includes a container holding a therapeutically effective amount of at least one lipoxin compound having one of the formulae described above and instructions for using the lipoxin compound for treating an PMN responsive state in the subject.

In preferred embodiments, $Y_1$ is a hydroxyl and the carbon bearing the hydroxyl can have an R or S configuration. In most preferred embodiments, the chiral carbon bearing the hydroxyl group, e.g., $Y_1$ is designated as a 15-epi-lipoxin as is known in the art.

In certain embodiments the chirality of the carbons bearing the $R_2$, $R_3$, $Q_3$ and $Q_4$ groups can each independently be either R or S. In preferred embodiments, $Q_3$ and $Q_4$ have the chiralities shown in structures II, III, IV or V.

In preferred embodiments, $R_4$ is a hydrogen. In other preferred embodiments, $R_6$ is a hydrogen.

Additionally, $R_5$ can be a substituted or unsubstituted, branched or unbranched alkyl group having between 1 and about 6 carbon atoms, preferably between 1 and 4 carbon atoms, most preferably between 1 and 3, and preferably one or two carbon atoms. The carbon atoms can have substituents which include halogen atoms, hydroxyl groups, or ether groups.

The compounds encompassed by U.S. Pat. No. 5,441,951 are excluded from certain aspects of the present invention.

The compounds useful in the present invention can be prepared by the following synthetic scheme:

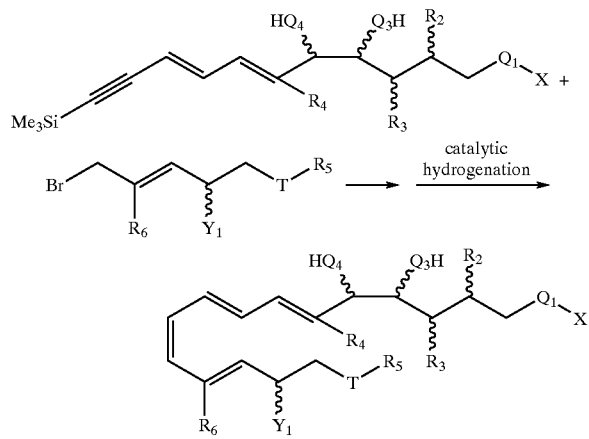

wherein X, $Q_1$, $Q_3$, $Q_4$, $R_2$, $R_3$, $R_4$, $R_5$, $R_6$, $Y_1$ and T are as defined above. Suitable methods known in the art to can be used to produce each fragment. For example, the acetylenic fragment can be prepared by the methods discussed in Nicolaou, K. C. et al. (1991) Angew. Chem. Int. Ed. Engl. 30:1100; Nicolaou, K. C. et al. (1989) J. Org. Chem. 54:5527; Webber, S. E. et al. (1988) Adv. Exp. Med. Biol. 229:61; and U.S. Pat. No. 5,441,951. The second fragment can be prepared by the methods of Raduchel, B. and Vorbruggen, H. (1985) Adv. Prostaglandin Thromboxane Leukotriene Res. 14:263.

A "lipoxin analog" shall mean a compound which has an "active region" that functions like the active region of a "natural lipoxin", but which has a "metabolic transformation region" that differs from natural lipoxin. Lipoxin analogs include compounds which are structurally similar to a natural lipoxin, compounds which share the same receptor recognition site, compounds which share the same or similar lipoxin metabolic transformation region as lipoxin, and compounds which are art-recognized as being analogs of lipoxin. Lipoxin analogs include lipoxin analog metabolites. The compounds disclosed herein may contain one or more centers of asymmetry. Where asymmetric carbon atoms are present, more than one stereoisomer is possible, and all possible isomeric forms are intended to be included within the structural representations shown. Optically active (R) and (S) isomers may be resolved using conventional techniques known to the ordinarily skilled artisan. The present invention is intended to include the possible diastereoiomers as well as the racemic and optically resolved isomers.

The terms "corresponding lipoxin" and "natural lipoxin" refer to a naturally-occurring lipoxin or lipoxin metabolite.

Where an analog has activity for a lipoxin-specific receptor, the corresponding or natural lipoxin is the normal ligand for that receptor. For example, where an analog is a $LXA_4$ specific receptor on differentiated HL-60 cells, the corresponding lipoxin is $LXA_4$. Where an analog has activity as an antagonist to another compound (such as a leukotriene), which is antagonized by a naturally-occurring lipoxin, that natural lipoxin is the corresponding lipoxin.

"Active region" shall mean the region of a natural lipoxin or lipoxin analog, which is associated with in vivo cellular interactions. The active region may bind the "recognition site" of a cellular lipoxin receptor or a macromolecule or complex of macromolecules, including an enzyme and its cofactor. Preferred lipoxin $A_4$ analogs have an active region comprising $C_5$–$C_{15}$ of natural lipoxin $A_4$. Preferred lipoxin $B_4$ analogs have an active region comprising C5–C14 of natural lipoxin B4.

The term "recognition site" or receptor is art-recognized and is intended to refer generally to a functional macromolecule or complex of macromolecules with which certain groups of cellular messengers, such as hormones, leukotrienes, and lipoxins, must first interact before the biochemical and physiological responses to those messengers are initiated. As used in this application, a receptor may be isolated, on an intact or permeabilized cell, or in tissue, including an organ. A receptor may be from or in a living subject, or it may be cloned. A receptor may normally exist or it may be induced by a disease state, by an injury, or by artificial means. A compound of this invention may bind reversibly, irreversibly, competitively, noncompetitively, or uncompetitively with respect to the natural substrate of a recognition site.

The term "metabolic transformation region" is intended to refer generally to that portion of a lipoxin, a lipoxin metabolite, or lipoxin analog including a lipoxin analog metabolite, upon which an enzyme or an enzyme and its cofactor attempts to perform one or more metabolic transformations which that enzyme or enzyme and cofactor normally transform on lipoxins. The metabolic transformation region may or may not be susceptible to the transformation. A nonlimiting example of a metabolic transformation region of a lipoxin is a portion of $LXA_4$ that includes the C-13,14 double bond or the C-15 hydroxyl group, or both.

The term "detectable label molecule" is meant to include fluorescent, phosphorescent, and radiolabeled molecules used to trace, track, or identify the compound or receptor recognition site to which the detectable label molecule is bound. The label molecule may be detected by any of the several methods known in the art.

The term "labeled lipoxin analog" is further understood to encompass compounds which are labeled with radioactive isotopes, such as but not limited to tritium ($^3$H), deuterium ($^2$H), carbon ($^{14}$C), or otherwise labeled (e.g. fluorescently). The compounds of this invention may be labeled or derivatized, for example, for kinetic binding experiments, for further elucidating metabolic pathways and enzymatic mechanisms, or for characterization by methods known in the art of analytical chemistry.

The term "inhibits metabolism" means the blocking or reduction of activity of an enzyme which metabolizes a native lipoxin. The blockage or reduction may occur by covalent bonding, by irreversible binding, by reversible binding which has a practical effect of irreversible binding, or by any other means which prevents the enzyme from operating in its usual manner on another lipoxin analog, including a lipoxin analog metabolite, a lipoxin, or a lipoxin metabolite.

The term "resists metabolism" is meant to include failing to undergo one or more of the metabolic degradative transformations by at least one of the enzymes which metabolize lipoxins. Two nonlimiting examples of $LXA_4$ analog that resists metabolism are 1) a structure which can not be oxidized to the 15-oxo form, and 2) a structure which may be oxidized to the 15-oxo form, but is not susceptible to enzymatic reduction to the 13,14-dihydro form.

The term "more slowly undergoes metabolism" means having slower reaction kinetics, or requiring more time for the completion of the series of metabolic transformations by one or more of the enzymes which metabolize lipoxin. A nonlimiting example of a $LXA_4$ analog which more slowly undergoes metabolism is a structure which has a higher transition state energy for C-15 dehydrogenation than does $LXA_4$ because the analog is sterically hindered at the C-16.

The term "tissue" is intended to include intact cells, blood, blood preparations such as plasma and serum, bones, joints, muscles, smooth muscles, and organs.

The term "halogen" is meant to include fluorine, chlorine, bromine and iodine, or fluoro, chloro, bromo, and iodo. In certain aspects, the compounds of the invention do not include halogenated compounds, e.g., fluorinated compounds.

The term "subject" is intended to include living organisms susceptible to conditions or diseases caused or contributed to by inflammation, inflammatory responses, vasoconstriction, and myeloid suppression. Examples of subjects include humans, dogs, cats, cows, goats, and mice. The term subject is further intended to include transgenic species.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiment, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters. In a preferred embodiment, the ester is not a methyl ester (See, for example, Berge et al., supra.).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Materials and Methods

Biostability of LX analogs in mouse whole blood. The analogs $ATLa_1$ and $ATLa_2$ were prepared by total organic synthesis and their structures confirmed by NMR (Serhan, C. N., Maddox, J. F., Petasis, N. A., Akritopoulou-Zanze, I., Papayianni, A., Brady, H. R., Colgan, S. P. & Madara, J. L. (1995) Biochemistry 34, 14609–14615) (See also U.S. Pat. Nos. 5,441,951, 5,648,512, 5,650,435 and 5,750,354, incoporated herein by reference, for suitable examples of syntheses). Male BALB/c mice (6–8 wk) (Harlan Sprague Dawley, Inc.) were anesthetized with pentobarbital (70 mg/kg) and whole blood was drawn via cardiac puncture into heparin (500 U/ml). $LXA_4$, $ATLa_1$, and $ATLa_2$ (2.4 $\mu$M) were incubated in 250 $\mu$l of blood (37° C.) for either 0 or 3 h. For time zero (T=0), the blood aliquots were placed in an ice bath for 1 min and, immediately after the addition of $LXA_4$ or ATLa, were centrifuged at 800×g at 0° C. for 20 min. The plasma supernatants were collected, stopped in 400 pl of ice cold methanol, and stored at −20 ° C. prior to solid phase extraction. For T=3 h, the blood aliquots were incubated with ATLa and gently mixed by shaking at 37° C. After each incubation period, the plasma was collected and stopped as above. Prostaglandin $B_2$ (Oxford Biomedical Research, Inc., Oxford, Mich.) was added to the blood samples immediately before centrifugation as an internal standard for extraction recovery. Denatured protein precipitates were pelleted from the stopped plasma samples and were washed twice with 200 $\mu$l of methanol. The plasma supernatant and washes were pooled and extracted with Extract—Clean solid phase extraction cartridges (500 mg $C_{18}$, Alltech Associates Inc., Deerfield, Ill.). The methyl formate fractions were taken to dryness with a gentle stream of nitrogen and suspended in methanol for injection and quantitative analyses by UV spectrophotometry and LC/MS/MS.

LC/MS/MS analyses. LC/MS/MS was performed employing an LCQ (Finnigan MAT, San Jose, Calif.) quadrupole ion trap mass spectrometer system equipped with an electrospray atmospheric pressure ionization probe. Samples were suspended in methanol and injected into the HPLC component, which consisted of a SpectraSYSTEM P4000 (Thermo Separation Products, San Jose, Calif.) quaternary gradient pump, a Prodigy octadecylsilane-3 (100×2 mm, 5 $\mu$m) column (Phenomenex, Torrance, Calif.) or a LUNA C18-2 (150×2 mm, 5 $\mu$m) column, and a rapid spectra scanning SpectraSYSTEM UV2000 (Thermo Separation Products, San Jose, Calif.) UV/VIS absorbance detector. The column was eluted isocratically with methanol/water/acetic acid (65:35:0.01, v/v/v) at 0.2 ml/min into the electrospray probe. The spray voltage was set to 5–6 kV and the heated capillary to 250° C. $LXA_4$ and the ATLa were quantitated by selected ion monitoring (SIM) for analyte molecular anions (e.g. $[M-H]^-$=m/z 351.5 for $LXA_4$, m/z 365.5 for $ATLa_1$, and m/z 405.5 for $ATLa_2$ free acid) or by UV absorbance at 300 nm. Product ion mass spectra (MS/MS) were also acquired for definitive identification of the compounds.

PMN infiltration into mouse air pouch. While male BALB/c mice (6–8 wk) were anesthetized with isoflurane, dorsal air pouches were raised by injecting 3 ml of sterile air subcutaneously on days 0 and 3 (as in ref.) (Sin, Y. M., Sedgwick, A. D., Chea, E. P. & Willoughby, D. A. (1986) Ann. Rheum. Dis. 45, 873–877). On day 6 and while the mice were anesthetized with isoflurane, 10 $\mu$g of $ATLa_2$ was delivered as a bolus injection into either the tail vein in 100 $\mu$l of sterile 0.9% saline or locally into the air pouch in 900 $\mu$l of PBS −/− (Dulbecco's Phosphate Buffered Saline without magnesium or calcium ions, BioWhittaker, Walkersville, Md.). Dexamethasone and ASA (Sigma Chemical Co., St. Louis, Mo.) were delivered locally as 10 μg and 1.0 mg doses in 900 μl of PBS –/–, respectively. Inflammation in the air pouch was induced by local injection of recombinant murine TNF-α(20 ng) (Boehringer Mannheim, Indianapolis, Id.) dissolved in 100 μl of sterile PBS. While the mice were anesthetized with isoflurane, the air pouches were lavaged twice with 3 ml of sterile PBS 4 h after the initial TNF-α injection. Aspirates were centrifuged at 2000 rpm for 15 min at 23° C. The supernatants were removed and the cells were suspended in 500 μl of PBS. Aliquots of the cell suspension were stained with Trypan Blue and enumerated by light microscopy. 50 μl of the resuspended aspirate cells were added to 150 μl of 30% BSA and centrifuged onto microscope slides at 2200 rpm for 4 min using a Cytofuge (StatSpin, Norwood, Mass.). Slides were allowed to air dry and were stained with Wright Giemsa stain (Sigma Chemical Co., St. Louis, Mo.) for determination of differential leukocyte counts. For microscopic analysis, tissues were obtained with a 6 mm tissue biopsy punch (Acu-Punch, Acuderm, Inc., Ft. Lauderdale, Fla.) and fixed in 10% buffered formaldehyde. Samples were then embedded in paraffin, sliced, and stained with hematoxylin-eosin.

Arterial pressure. Male BALB/c mice (6–8 wk, 20 g) were anesthetized with pentobarbital (80 mg/kg). The trachea was isolated and a small polyethylene catheter (PE50) was introduced to maintain a patent airway. The right carotid artery was isolated and cannulated with PE10 tubing filled with heparinized (10 units/ml) normal saline. The arterial catheter was connected to a pressure transducer (World Precision Instruments, Sarasota, FA) and the arterial pressure tracing was recorded continuously (Astromed MT95K2, West Warwick, R.I.). All surgical manipulations were performed using a surgical microscope (Carl Zeiss, Inc., Thornwood, N.Y.).

PMN infiltration into ear skin. The mouse ear inflammation model was used to evaluate the impacts of i.v. and topical deliveries of ATLa$_2$ on LTB$_4$- and PMA-induced PMN infiltration (Takano, T., Clish, C. B., Gronert, K., Petasis, N. & Serhan, C. N. (1998) *J. Clin. Invest.* 101, 819–826). Briefly, ATLa$_2$ was either applied topically (20 μg in 10 μl acetone) to the inner side of the left mouse ear with vehicle applied contralaterally, or delivered as a bolus injection (10 μg in 100 μl of 0.9% sterile saline) through the tail vein. 5–7 min later, inflammation was induced in left and right ears of the mice that received topical ATLa$_2$ (left ear only in the mice receiving i.v. delivery of ATLa$_2$) by topical application of either LTB$_4$ (1 μg) or PMA (100 ng) in acetone (10 μl). After 24 h, 6 mm diameter tissue punch biopsies were taken (Acu-Punch, Acuderm, Inc., Ft. Lauderdale, Fla.) from the ears and assayed by the method of Bradley et al. for myeloperoxidase (MPO) activity as an index of PMN number. Isolated murine PMN were enumerated by light microscopy and processed in the same manner to obtain a calibration curve (Bradley, P. P., Priebat, D. A., Christensen, R. D. & Rothstein, G. (1982) *J. Invest. Dermatol.* 78, 206–209).

Plasma clearance. The time course for the clearance of ATLa$_2$ from plasma following tail vein injection was determined over 50 min. Male BALB/c mice (6–8 wk, 20 g) were anesthetized with pentobarbital (70 mg/kg) and received bolus tail vein injections of 27 μM ATLa$_2$ (0.1 mg/kg) in 100 μl of sterile 0.9% saline. Blood was taken from the mice by cardiac puncture at 2, 5, 10, 15, and 50 min post-injection. The plasma was obtained and extracted as a above, with the methyl formate fractions from the solid phase extraction being dried down for LC/MS/MS analysis. Values for ATLa$_2$ quantified in plasma are expressed in units of ng/ml plasma taken from the mouse, with n=3 for each time point.

Results

Biostability of LX stable analogs. Following 3 h incubations of LXA$_4$ in mouse whole blood ex vivo, the predominant metabolite peak observed in the LC/MS chromatogram of the extracted sample had a retention time and MS/MS spectrum matching that of 15-oxo-LXA$_4$, as generated by recombinant 15-PGDH from synthetic LXA$_4$ (FIG. 1A). To determine whether addition of bulky substituents to the native LX structure enhances biostability, two aspirin-triggered lipoxin stable analogs, 15(R/S)-methyl-LXA$_4$ (ATLa$_1$) and 15-epi-16-(para-fluoro)-phenoxy-LXA$_4$ (ATLa$_2$), were incubated in mouse whole blood and compared to LXA$_4$. A methyl group at carbon-15 was placed as a racemate to protect both LXA$_4$ and 15-epi-LXA$_4$ in ATLa$_1$ and a fluoride was placed at the para-position of the phenoxy ring of 15-epi-16-phenoxy-LXA$_4$ in ATLa$_2$ (FIG. 1B). LC/MS/MS analysis of whole blood incubations showed that ~40% of LXA$_4$ was lost while both ATLa$_1$ and ATLa$_2$ exhibited greater stability with ~90% and ~100% remaining, respectively (FIG. 1B). In human whole blood, quantitatively similar results were obtained with ATLa$_1$.

Figure 2:
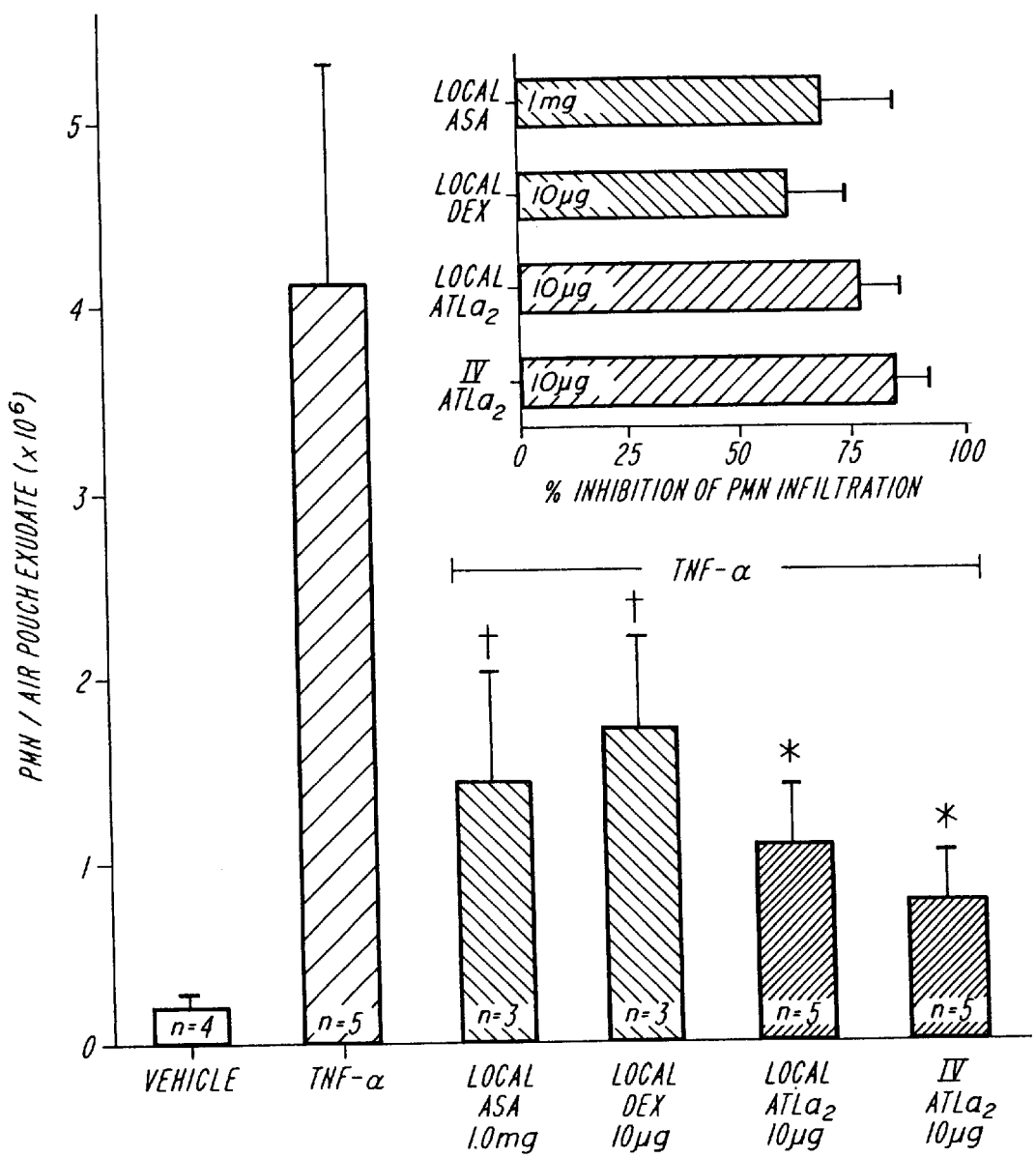
FIG. 2 demonstrates that $ATLa_2$ inhibits TNF-α-induced PMN infiltration by both local air pouch and i.v. delivery. When injected locally into the air pouch, following injection of vehicle (900 μl PBS), murine TNF-α (20 ng/100 μl PBS) induced the infiltration of 4.8±1.1×10$^6$ PMN by 4 h. Dexamethasone (10 μg/air pouch), ASA (1 mg/air pouch), and $ATLa_2$ (10 μg/air pouch) were locally administered in 900 μl PBS and prior to TNF-α. Systemic delivery of $ATLa_2$ was by i.v. injection into the mouse tail vein (10 μg/mouse). 2.1±0.7×10$^5$ PMN were found in the air pouch 4 h after injection of vehicle (1 ml sterile PBS) alone. Values represent mean±SEM (n=3–5). *P<0.05, †P<0.15 Student's two-tailed t-test.

Intravenous and local delivery of ATLa$_2$ inhibits TNF-α-induced PMN infiltration in the dorsal air pouch. The six day murine dorsal air pouch is characterized by the presence of a nascent lining that encloses the air cavity and is composed of both fibroblast-like cells, which are indistinguishable from type B cells of murine knee synovium, and macrophage-like cells, which share morphology with synovial type A cells (Edwards, J. C. W., Sedgwick, A. D. & Willoughby, D. A. (1981) *J. Pathol.* 134, 147–156). The air pouch therefore serves as an in vivo model of the rheumatoid synovium and was used here to evaluate the impact of intravenous and local delivery of ATLa$_2$ in the inhibition of cytokine-mediated inflammation, and for direct comparison to the actions of ASA and dexamethasone (Sin, Y. M., Sedgwick, A. D., Chea, E. P. & Willoughby, D. A. (1986) *Ann. Rheum. Dis.* 45, 873–877; Edwards, J. C. W., Sedgwick, A. D. & Willoughby, D. A. (1981) *J. Pathol.* 134, 147–156). Tumor necrosis factor-α (TNF-α) induces leukocyte infiltration, predominantly neutrophils (>75%), into the pouch with maximal cell accumulation occurring between 2–4 h post-injection (Tessier, P. A., Naccache, P. H., Clark-Lewis, I., Gladue, R. P., Neote, K. S. & McColl, S. R. (1997) *J. Immunol* 159, 3595–3602). ATLa$_2$, dexamethasone, and ASA were each injected locally into the air pouch of individual mice and immediately prior to the administration of murine TNF-α. For systemic delivery of ATLa$_2$, injections were given via the mouse tail vein before local air pouch injection of murine TNF-α. Here, local delivery of TNF-αalone (20 ng/mouse) induced the recruitment of 4.8× 1.1±10$^6$ PMN into the air pouch at 4 h (FIG. 2). When ATLa$_2$ was delivered locally into the air pouch (10 μg/mouse), only 1.1±0.3×10$^6$ PMN were present in the pouch exudate, representing ~77% inhibition of the TNF-α-induced PMN infiltration. Delivery of ATLa$_2$ (10 μg/mouse) by i.v. injection proved to be an even more potent method of inhibiting TNF-α-driven PMN infiltration. The PMN recruitment values dropped to an average of 7.9±2.9× 10$^5$ PMN/air pouch, representing an inhibition of ~85%. Moreover, no apparent toxicity of ATLa$_2$ to the mice was observed. Local administration of either ASA or dexamethasone also inhibited PMN recruitment, but to a lesser extent than ATLa$_2$ by either local or i.v. delivery. An equivalent dose of dexamethasone (10 μg/mouse) led to 61% inhibition of PMN recruitment (infiltration of 1.7±0.5×10$^6$ PMN), whereas a 100-fold greater dose of ASA (1.0 mg/mouse) was required to inhibit PMN infiltration to a similar degree as ATLa$_2$. The presence of 1.5±0.6 ×10$^6$ cells with 1.0 mg ASA represents 69% inhibition compared to TNF-α administration alone given to mice in parallel.

Figure 3A:
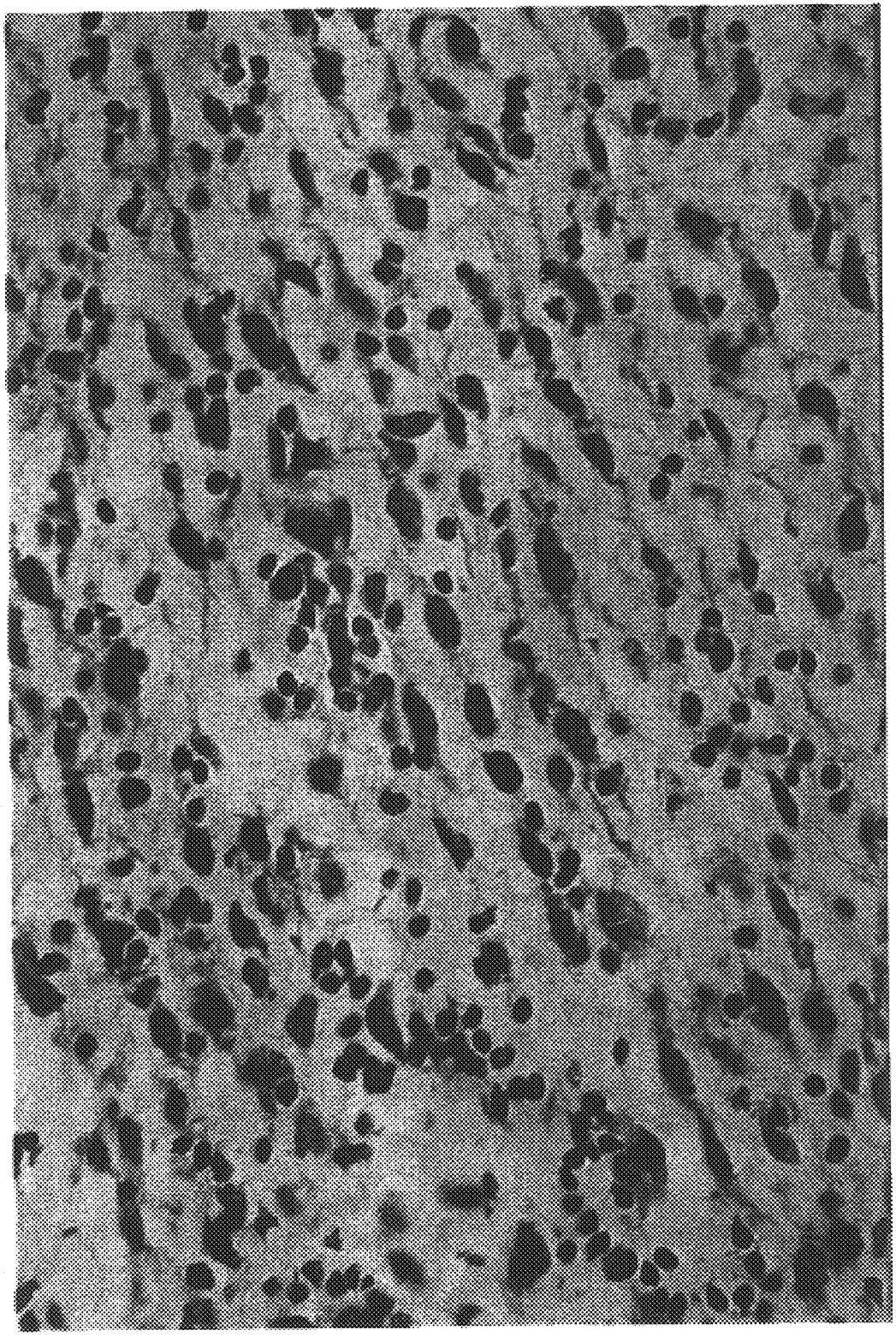
FIG. 3 are representative tissue biopsies of air pouch linings: inhibition of TNF-α-induced PMN accumulation. (A) Lining section taken 4 h after exposure to TNF-α (20 ng/mouse) showing increased neutrophil number, low-power field inset. (B) Section taken 4 h following exposure to TNF-α (20 ng/mouse), with prior local delivery of $ATLa_2$ (10 μg/mouse). (C) Section taken 4 h following exposure to TNF-α (20 ng/mouse), with prior i.v. delivery of $ATLa_2$ (10 μg/mouse). (D) Section of 6-day air pouch lower lining taken from a mouse 4 h following exposure to vehicle alone. Arrows denote neutrophils. Sections were prepared as in Methods and stained with hematoxylin-eosin.
Figure 3B:
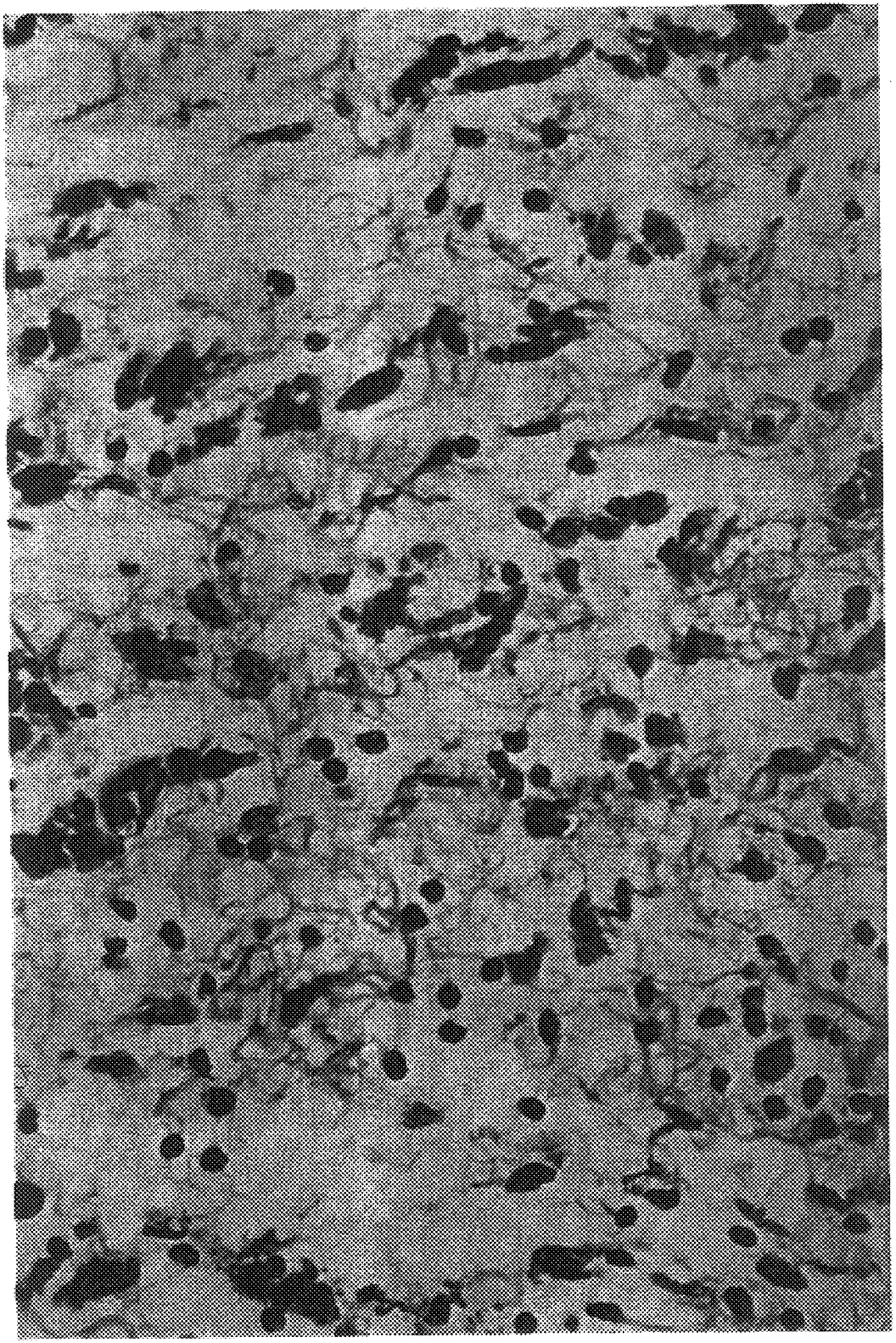
Figure 3C:
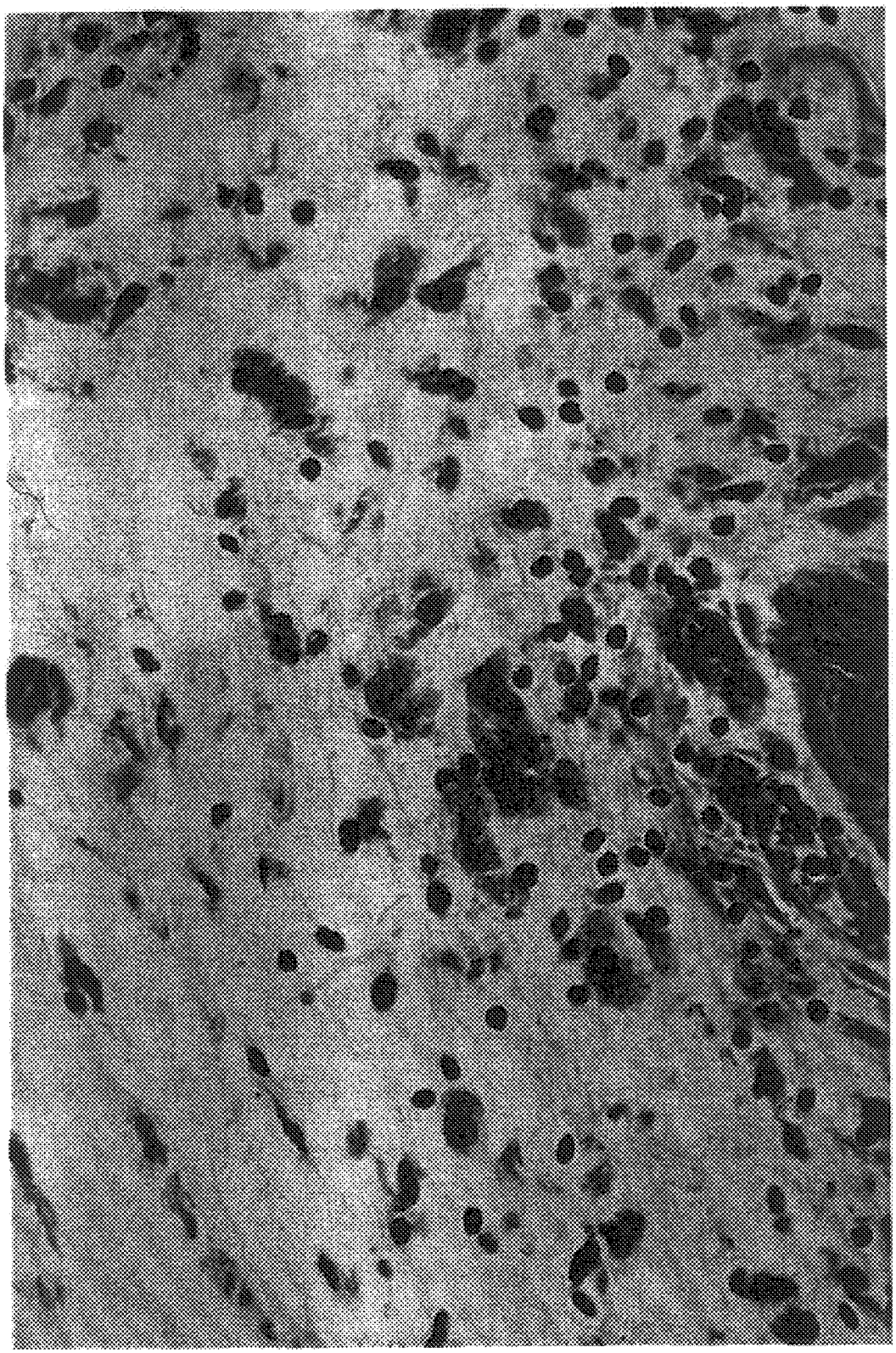
Figure 3D:
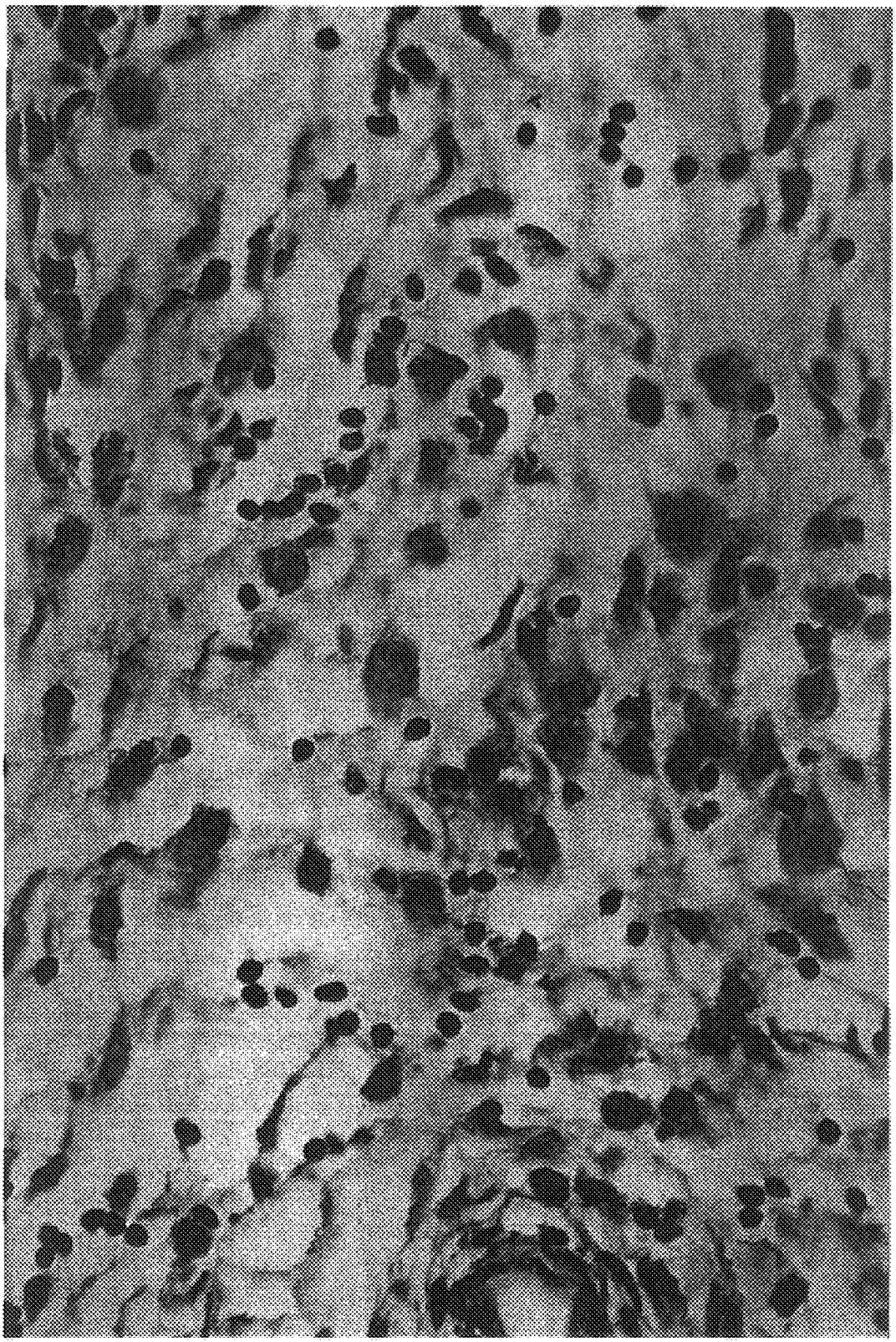

Histological analysis of the tissue lining surrounding the air pouch cavity showed that the addition of TNF-α resulted in a markedly increased number of neutrophils (FIG. 3A), which was reduced when ATLa$_2$ was delivered by either intra-pouch injection (FIG. 3B) or i.v. via the tail vein (FIG. 3C) prior to TNF-α administration. Moreover, microscopic analyses of dermal tissue from mice that received ATLa$_2$ treatment were indistinguishable from those exposed only to vehicle (FIG. 3D), which also showed a mild neutrophil infiltrate accompanying this wound model.

Figure 4:
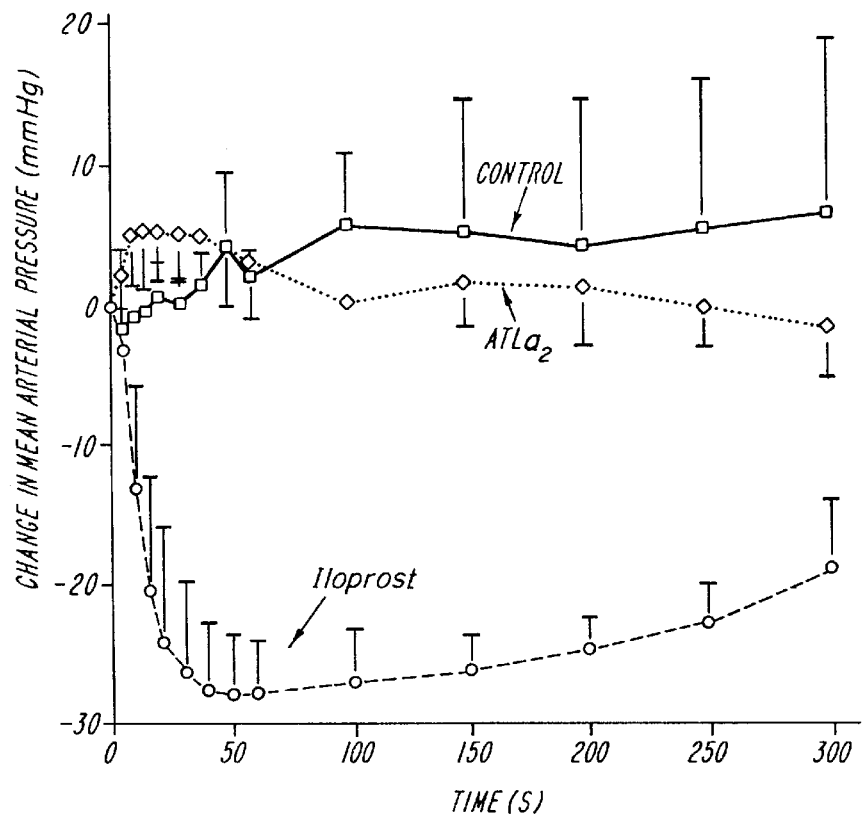
FIG. 4 demonstrates that $ATLa_2$ does not inhibit PMN recruitment to a site of inflammation by regulating vasodilatation. Mouse arterial pressure was monitored with a pressure transducer via the cannulated carotid artery. Tail vein injection of vehicle (100 μl; 0.9% saline) showed no changes in arterial pressure while 10 μg Iloprost elicited a maximum mean decrease of ~28 mmHg ~50 s post-injection, with pressure returning to baseline after ~500 s. 10 μg of $ATLa_2$ were injected into 3 mice with no change in mean arterial pressure. Values represent mean±SEM (n=3).

ATLa$_2$ does not inhibit PMN recruitment by regulating vasoactivity. LXA$_4$ exhibits both concentration- and vascular bed-dependent vasoactive properties. For example, topical administration of LXA$_4$ (1 μM) induces arteriolar dilation in the hamster cheek with no change in venular diameters while systemic delivery into rats produces a vasoconstrictor response in the mesenteric bed (26). In addition, 20 min infusion of 1 or 2 μg/kg LXA$_4$ induces renal vasorelaxation in rats without changing mean arterial pressure (27). To determine whether the increased stability of ATLa$_2$ enhances potential vasoreactivity at the therapeutic dose found to inhibit PMN infiltration in FIGS. 2 and 5, vascular changes in response to ATLa$_2$ were compared directly to those of Iloprost, a prostacyclin stable analog that rapidly stimulates arterial vasodilation (Grant, S. M. & Goa, K. L. (1992) *Drugs* 43, 899–924). Added to organ baths, ATLa$_2$ relaxed precontracted isolated rat aorta to ~40% of the level of relaxation caused by equimolar treatment (1 μM) with Iloprost (not shown). However, when 10 μg, or ~24 nmol/mouse, of ATLa$_2$ were injected into the tail vein as in FIG. 2, no apparent changes in mean arterial pressure were observed (FIG. 4). In sharp contrast, injection of equimolar quantities of Iloprost elicited a maximum mean decrease of ~28 mmHg ~50 s post-injection, with pressure returning to baseline after 8 min.

Figure 5:
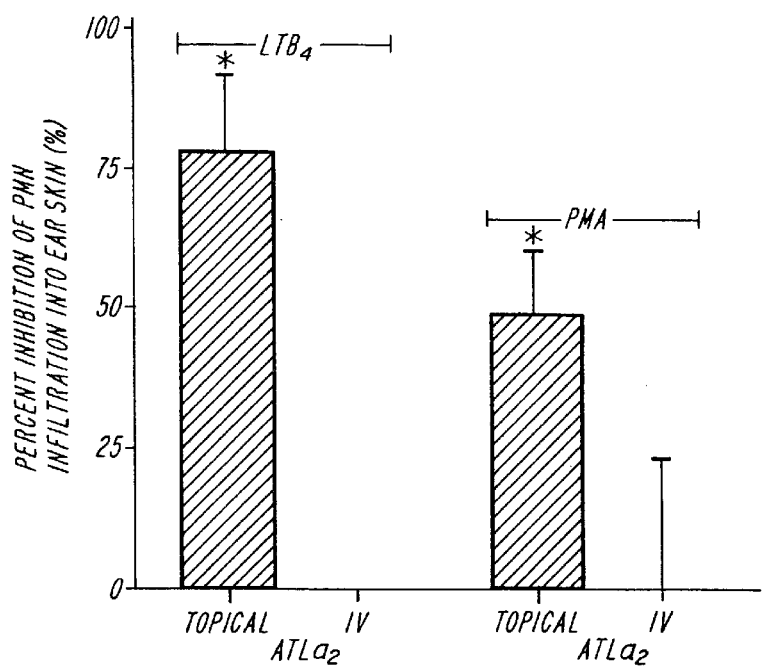
FIG. 5 demonstrates that $ATLa_2$ inhibits both PMA- and $LTB_4$-induced PMN infiltration by topical application and not i.v. injection. $ATLa_2$ was applied topically (20 μg in 10 μl acetone) to the left mouse ear or delivered intravenously (10 μg in 100 μl of 0.9% sterile saline) through the tail vein. Inflammation was induced in left and right ears by topical application of either $LTB_4$ (1 μg) or PMA (100 ng) in acetone (10 μl). Punch biopsies were obtained after 24 h and MPO activity was measured as an index of PMN number in the ear. Values represent mean±SEM (n=3). *P<0.05 Student's two-tailed t-test.

ATLa$_2$ inhibits PMN infiltration in murine ear skin to both exogenous and endogenous chemoattractants. Topical application of a racemic analog with properties of both 15-epi-LXA$_4$ and native LXA$_4$, and 16-phenoxy-LXA$_4$ (an analog of LXA$_4$) to mouse ear epidermis inhibits LTB$_4$-induced PMN influx as well as vascular permeability changes (Takano, T., Clish, C. B., Gronert, K., Petasis, N. & Serhan, C. N. (1998) *J. Clin. Invest.* 101, 819–826). Here, this ear skin model of inflammation was used to determine whether i.v. or topical delivery of the whole blood stable ATLa$_2$ could also inhibit PMN influx, which is maximal at 24 h after topical application of either LTB$_4$ or phorbol myristate acetate (PMA) to skin. Topical application of ATLa$_2$ inhibited both LTB$_4$-and PMA-induced inflammation, by ~78% and 49% respectively (FIG. 5). A single bolus i.v. injection of ATLa$_2$ (10 μg) did not inhibit PMN influx measured at 24 h to either agonist applied topically to ear skin (FIG. 5) in contrast to i.v. and dorsal administration in the air pouch (FIG. 2). But, when i.v. injection of this analog was repeated at 20h (4h before PMN measurement), LTB$_4$-induced PMN recruitment was inhibited by ~22% (not shown).

Figure 6:
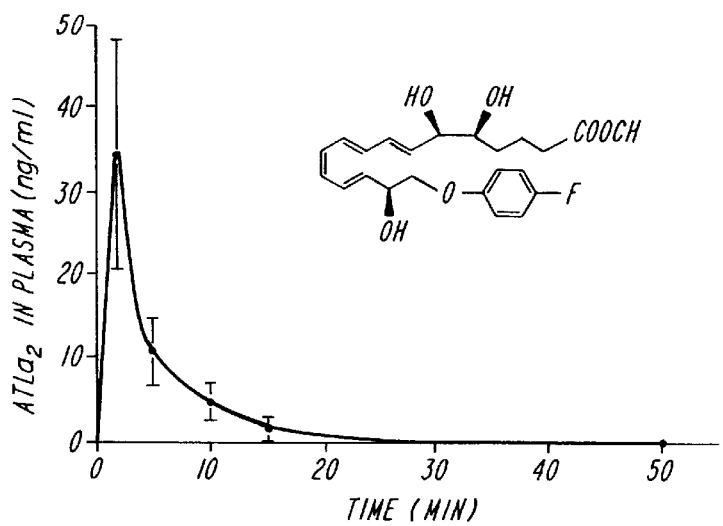
FIG. 6 depicts $ATLa_2$ bolus tail vein injection: time course in plasma. BALB/c mice (6–8 wk) received i.v. tail vein injections of $ATLa_2$ (2 μg/mouse) in 100 μl sterile 0.9% saline. Blood was obtained by cardiac puncture and $ATLa_2$ was extracted from the plasma by solid phase extraction. The amounts of $ATLa_2$ remaining were quantitated by LC/MS/MS. Values represent mean±SEM (n=3).
Figure 7:
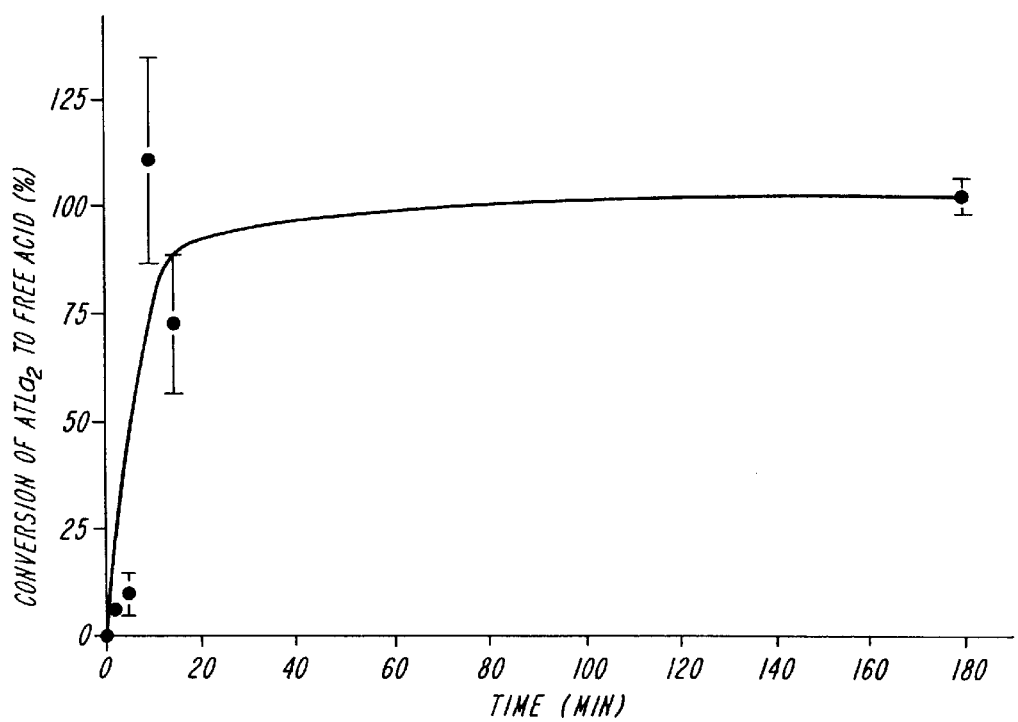
FIG. 7 represents methyl ester hydrolysis of $ATLa_2$ to free acid in ex vivo mouse whole blood. ATLa2 was incubated ex vivo in mouse whole blood (2.8 μM) for 0, 2, 5, 10, 15, or 180 minutes. The incubations were stopped by chilling the blood on ice for one minute followed by centrifugation (800 ×g) at 0° C. The plasma supernatant was stopped in 2 vol of ice cold methanol. The samples were prepared for analysis by solid phase extraction and the amount of free acid in the sample was quantiitated by LC/MS/MS. Within 10–15 minutes, 100% of the $ATLa_2$ methyl ester is hydrolyzed to the free acid without loss of compound. Values represent mean±SEM (n=3).
Figure 8:
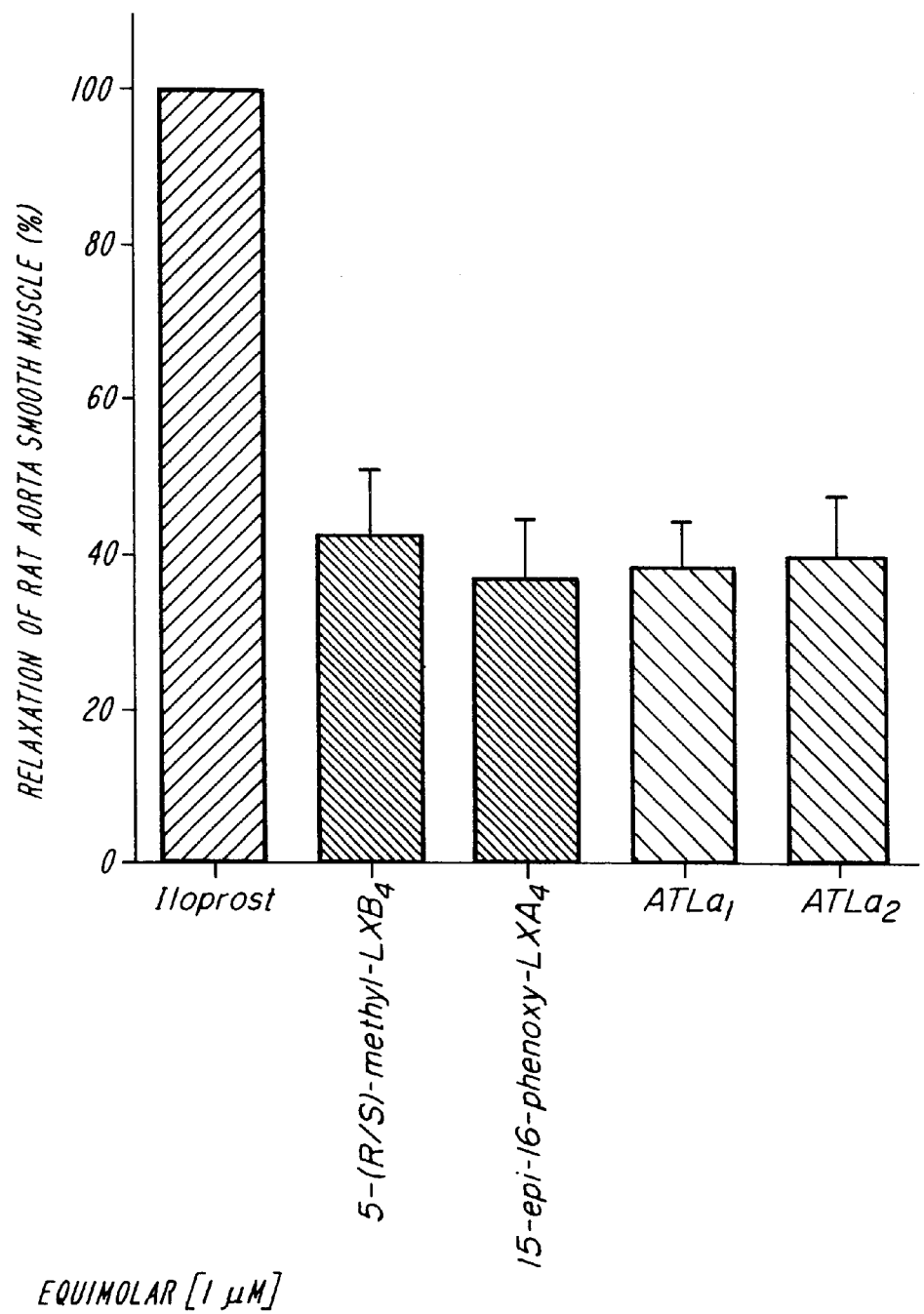
FIG. 8 demonstrates that ATL analogs induce vasodilation in isolated rat aorta: relaxation relative to Iloprost. Rats were euthanized with pentobarbital overdoses. The aorta was isolated and a pre-load of 300–400 mg given. The vessels were pre-contracted with U46619 (25 ng/ml). Relaxation was induced with addition of Iloprost, 5(R/S)-methyl-$LXB_4$, $ATLa_1$,or $ATLa_2$ to a final concentration of μM. Aorta smooth muscle relaxation was measured with a force transducer and the data digitized and stored on a PC. 5(R/S)-methyl-$LXB_4$, $ATLa_1$, and $ATLa_2$ caused 42.8%, 37.0%, 38.1%, and 40.0% relaxation of smooth muscle, respectively. Values represent±SEM (n=4–6).

ATLa$_2$ is rapidly cleared from plasma following i.v. injection. Since i.v. tail vein delivery of ATLa$_2$ elicited a potent anti-inflammatory response blocking PMN infiltration within a 4 h period in the dorsal air pouch (FIG. 2) but not at 24 h in the ear skin (FIG. 5), the question arose as to what extent ATLa$_2$ possessed enhanced biostability in circulation following bolus tail vein injections. To address this, ATLa$_2$ was extracted from mouse plasma collected at several time intervals following tail vein injections and the recovered materials were quantitated by LC/MS/MS. At 2 min post-injection, ~34 ng/ml plasma were detected. The levels of the analog decreased with time and were not detected after 15 min. These results indicate rapid clearance from blood and therefore rapid distribution and/or elimination (FIG. 6).

The fluorinated analog of 15-epi-LXA$_4$, ATLa$_2$, is a novel stable analog inhibitor of both direct (LTB$_4$) and indirect (TNF-α, PMA) acting chemoattractants. These in vivo observations further support the role of the aspirin-triggered lipoxin circuit as a novel and additional mechanism underlying aspirin's anti-inflammatory therapeutic impact and provide evidence for endogenous anti-inflammatory signaling pathways.

The present results indicate that specific design modifications of the native LXA$_4$ structure, such as the addition of a C-15 methyl group (ATLa$_1$) or a bulky ω-chain (para-fluoro)-phenoxy group (ATLa$_2$), prolong the lifetime in blood of these compounds and therefore, potentially, their bioavailabilities as well. Such modifications sterically hinder conversion of the analogs, relative to rapid bioinactivation of the native structure, by recombinant 15-PGDH in vitro (Serhan, C. N. (1997) *Prostaglandins* 53, 107–137). As evidenced by LC/MS/MS analyses, the major product of this human dehydrogenase incubated with LXA$_4$ is 15-oxo-LXA$_4$. LC/MS/MS analyses showed that 15-oxo-LXA$_4$ also was produced from LXA$_4$ in mouse whole blood (FIG. 1A), suggesting that the mouse shares with humans a common pathway for LXA$_4$ inactivation.

ATLa$_2$ proved to be a potent inhibitor of TNF-α-induced PMN infiltration into the air pouch cavity, as doses as low as 24 nmol/mouse delivered locally into the air pouch or by systemic i.v. injection via the tail vein resulted in ~77% and ~85% inhibition, respectively. Histologically, this wound model is thought to resemble rheumatoid synovium and TNF-α injection initiates PMN recruitment to the cavity (FIG. 2) (Edwards, J. C. W., Sedgwick, A. D. & Willoughby, D. A. (1981) *J. Pathol.* 134, 147–156). Injection of TNF-α into the air pouch increases, within the surrounding tissue, C—C chemokine (murine monocyte chemotactic peptide-1 and macrophage inflammatory protein-1α) and C—X—C chemokine (macrophage inflammatory protein-2) production and increases messenger RNA levels for the aforementioned chemokines as well as murine growth-related onco-gene protein-α; all of which are collectively required for neutrophil recruitment (Tessier, P. A., Naccache, P. H., Clark-Lewis, I., Gladue, R. P., Neote, K. S. & McColl, S. R. (1997) *J. Immunol* 159, 3595–3602). Since ATLa$_2$ blocked TNF-α-induced PMN infiltration (FIG. 2), ATL disrupts this chemokine network in vivo. This finding may have therapeutic implications, as a variety of pathological conditions, including rheumatoid arthritis, psoriasis, and Crohn's disease, have associated with them an over production of TNF-α, and therefore control of this cytokine's actions is highly sought (Marriott, J. B., Westby, M. & Dalgleish, A. G. (1997) *Drug Discovery Today* 2, 273–282).

It was also found that ATLa$_2$ was more potent than ASA since a 100-fold greater dose of ASA, delivered locally to the air pouch, resulted in a level of inhibition of TNF-α-driven PMN recruitment that was less than that of ATLa$_2$. Furthermore, a locally administered, equivalent dose of dexamethasone proved less potent as an inhibitor of PMN recruitment than ATLa$_2$ in this model. Given the unwanted side-effects associated with the structures of both ASA (acidity that can lead to ulceration) and dexamethasone (steroid structure that can also impact physiologic steroidal functions), structurally distinct compounds such as ATL analogs designed on the basis of endogenous regulators of leukocyte function may prove to be preferred therapeutic alternatives.

Applied topically to the ear, ATLa$_2$ also inhibited both LTB$_4$- and PMA-induced PMN recruitment, by ~78% and ~49%, respectively (FIG. 5). LXA$_4$ and ATLa$_1$ exhibit similar IC$_{50}$'s in vitro in the inhibition of PMN transmigration across polarized epithelial monolayers or PMN adherence to vascular endothelial cells (Takano, T., Clish, C. B., Gronert, K., Petasis, N. & Serhan, C. N. (1998) *J. Clin. Invest.* 101, 819–826). Topical delivery of ATLa$_1$ in vivo inhibits LTB$_4$-induced PMN recruitment, but interestingly the level of inhibition afforded by the native LXA$_4$ when added topically was less than 25% compared to that of either ATLa$_1$ or ATLa$_2$ (Takano, T., Clish, C. B., Gronert, K., Petasis, N. & Serhan, C. N. (1998) *J. Clin. Invest.* 101, 819–826). These observations regarding in vitro versus in vivo potencies between the analogs and the native structure indicate that the ATL analogs posses enhanced bioavailability in vivo. Thus, in addition to protection from enzymatic inactivation, the structural modifications to the native LXA$_4$ structure incorporated in ATLa$_1$ and ATLa$_2$ also improved their topical delivery and contributed to rapid distribution to tissue (FIG. 2).

Results obtained from the air pouch model, 4 h after administration of the analog, indicate that i.v. delivery of ATLa$_2$ to a remote site of inflammation was surprisingly even more effective than topical application. In sharp contrast are the findings with ear skin, where topical application of ATLa$_2$ elicited substantial inhibition of topically applied pro-inflammatory inflammatory mediators; i.v. delivery of the analog showed no apparent inhibition of LTB$_4$-induced PMN recruitment. It was also found that the ATL analog was both stable ex vivo in whole blood suspensions, with essentially completely quantitative recovery at 3 h, and was rapidly cleared from plasma following i.v. injection into the tail vein (between 15–50 min). Taken together, these results suggest that ATLa$_2$ is rapidly distributed to tissues from i.v. injections, rather than eliminated, and could remain in an active form for several hours, e.g. during the time course of the TNF-α-driven PMN recruitment to the wounded dorsal pouch (FIG. 2). Furthermore, the absence of PMN inhibition through systemic delivery in the mouse ear model indicates that ATLa$_2$ displays site selective bioaction from circulation, such as to the dorsal pouch rather than to ear skin.

In summary, these results indicate that the inhibitory actions of aspirin-triggered lipoxins are both tissue- and delivery site-dependent and are the first to show that stable analogs of ATL inhibit acute inflammation at sites distant from the point of delivery. Since ATL stable analogs were designed as mimetics to incorporate the native aspirin-triggered structural features, the present findings, taken together, provide new tools to examine endogenous anti-inflammatory pathways as well as avenues to approach the development of both topical and intravenous anti-PMN therapies.

REFERENCES

1. Weissmann, G. (1991) *Sci. Am.* 264, 84–90.
2. Ridker, P. M., Cushman, M., Stampfer, M. J., Tracy, R. P. & Hennekens, C. H. (1997) *N. Engl. J. Med.* 336, 973–979.
3. Marcus, A. J. (1995) *N. Engl. J. Med.* 333, 656–658.
4. Herschman, H. R. (1998) *Trends Cardiovasc. Med.* 8, 145–150.
5. Serhan, C. N. (1997) *Prostaglandins* 53, 107–137.
6. Chiang, N., Takano, T., Clish, C. B., Petasis, N. A., Tai, H.-H. & Serhan, C. N. (1998) *J. Pharmacol Exp. Ther.* 287, 779–790.
7. Lee, T. H., Crea, A. E., Gant, V., Spur, B. W., Marron, B. E., Nicolaou, K. C., Reardon, E., Brezinski, M. & Serhan, C. N. (1990) *Am. Rev. Respir. Dis.* 141, 1453–1458.
8. Chavis, C., Chanez, P., Vachier, I., Bousquet, J., Michel, F. B. & Godard, P. (1995) *Biochem. Biophys. Res. Commun.* 207,273–279.
9. Chavis, C., Vachier, I., Chanez, P., Bousquet, J. & Godard, P. (1996) *J. Exp. Med.* 183, 1633–1643.
10. Thomas, E., Leroux, J. L., Blotmnan, F. & Chavis, C. (1995) *Inflamm. Res.* 44, 121 –124.
11. Gewirtz, A. T., McCormick, B., Neish, A. S., Petasis, N. A., Gronert, K., Serhan, C. N. & Madara, J. L. (1998) *J. Clin. Invest.* 101, 1860–1869.
12. Pillinger, M. H. & Abramson, S. B. (1995) *Rheum. Dis. Clin. North Am.* 21, 691–714.
13. Hagihara, H., Nomoto, A., Mutoh, S., Yamaguchi, I. & Ono, T. (1991) *Atherosclerosis* 91, 107–116.
14. McLaughlan, J. M., Seth, R., Vautier, G., Robins, R. A., Scott, B. B., Hawkey, C. J. & Jenkins, D. (1997) *J. Pathol.* 181, 87–92.
15. Anezaki, K., Asakura, H., Honma, T., Ishizuka, K., Funakoshi, K., Tsukada, Y. & Narisawa, R. (1998) *Intern. Med.* 37,253–258.
16. Iverson, L. & Kragballe, K. (1997) in *Skin Immune System* (SIS), ed. Bos, J. D. (CRC Press, Boca Raton), pp. 227–237.
17. Ensor, C. M. & Tai, H.-H. (1991) in *Prostaglandins, Leukotrienes, Lipoxins, and PAF,* ed. Bailey, J. M. (Plenum Press, New York), pp. 39–52.
18. Serhan, C. N., Fiore, S., Brezinski, D. A. & Lynch, S. (1993) *Biochemistry* 32, 6313–6319.
19. Maddox, J. F., Colgan, S. P., Clish, C. B., Petasis, N. A., Fokin, V. V. & Serhan, C. N. (1998) *FASEB J.* 12,487–494.
20. Serhan, C. N., Maddox, J. F., Petasis, N. A., Akritopoulou-Zanze, I., Papayianni, A., Brady, H. R., Colgan, S. P. & Madara, J. L. (1995) *Biochemistry* 34, 14609–14615.
21. Takano, T., Clish, C. B., Gronert, K., Petasis, N. & Serhan, C. N. (1998) *J. Clin. Invest.* 101, 819–826.
22. Sin, Y. M., Sedgwick, A. D., Chea, E. P. & Willoughby, D. A. (1986)*Ann. Rheum. Dis.* 45, 873–877.
23. Bradley, P. P., Priebat, D. A., Christensen, R. D. & Rothstein, G. (1982) *J. Invest. Dermatol.* 78,206–209.
24. Edwards, J. C. W., Sedgwick, A. D. & Willoughby, D. A. (1981) *J. Pathol.* 134, 147–156.
25. Tessier, P. A., Naccache, P. H., Clark-Lewis, I., Gladue, R. P., Neote, K. S. & McColl, S. R. (1997) *J. Immunol.* 159, 3595–3602.
26. Dahlén, S. E. & Serhan, C. N. (1991) in *Lipoxygenases and their Products,* eds. Crooke, S. T. & Wong, A. (Academic Press, San Diego, Calif.), pp. 235–276.
27. Katoh, T., Takahashi, K., DeBoer, D. K., Serhan, C. N. & Badr, K. F. (1992) *Am. J. Physiol.* 263, F436–442.

28. Grant, S. M. & Goa, K. L. (1992) *Drugs* 43, 899–924.
29. Marriott, J. B., Westby, M. & Dalgleish, A. G. (1997) *Drug Discovery Today* 2, 273–282.

One of ordinary skill in the art will appreciate further features and advantages of the invention based on the above-described embodiments. Accordingly, the invention is not to be limited by what has been particularly shown and described, except as indicated by the appended claims. All publications and references cited herein, including those in the background section, are expressly incorporated herein by reference in their entirety.

What is claimed is:

1. A compound having the formula:

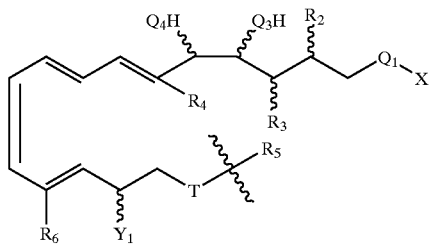

wherein X is $R_1$, $OR_1$, or $SR_1$;
wherein $R_1$ is
  (i) a hydrogen atom;
  (ii) an alkyl of 1 to 8 carbons atoms, inclusive, which may be straight chain or branched;
  (iii) a cycloalkyl of 3 to 10 carbon atoms;
  (iv) an aralkyl of 7 to 12 carbon atoms;
  (v) phenyl;
  (vi) substituted phenyl

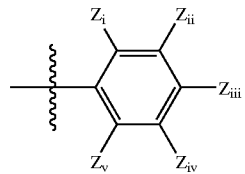

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
  (vii) a detectable label molecule; or
  (viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $Q_3$ and $Q_4$ are each independently O, S or NH;
wherein one of $R_2$ and $R_3$ is a hydrogen atom and the other is
  (a) H;
  (b) an alkyl of 1 to 8 carbon atoms, inclusive, which may be a straight chain or branched;
  (c) a cycloalkyl of 3 to 6 carbon atoms, inclusive;
  (d) an alkenyl of 2 to 8 carbon atoms, inclusive, which may be straight chain or branched; or
  (e) $R_aQ_2R_b$ wherein $Q_2$ is —O— or —S—; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$ is
  (a) H;
  (b) an alkyl of 1 to 6 carbon atoms, inclusive, which may be a straight chain or branched;
wherein $R_5$ is

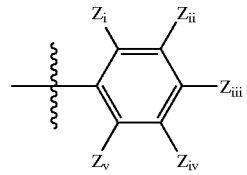

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;
wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;
wherein $R_6$ is
  (a) H;
  (b) an alkyl from 1 to 4 carbon atoms, inclusive, straight chain or branched;
wherein T is O or S, and pharmaceutically acceptable salts thereof, excluding 16-phenoxy-$LXA_4$ and 15-epi-16-(para-fluoro)-phenoxy-$LXA_4$.

2. A compound having the formula

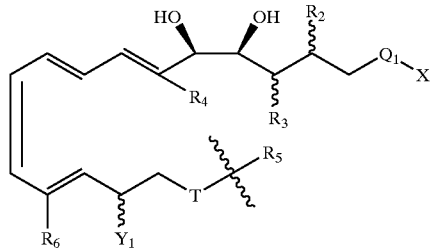

wherein X is $R_1$, $OR_1$, or $SR_1$;
wherein $R_1$ is
  (i) a hydrogen atom;
  (ii) an alkyl of 1 to 8 carbons atoms, inclusive, which may be straight chain or branched;
  (iii) a cycloalkyl of 3 to 10 carbon atoms;
  (iv) an aralkyl of 7 to 12 carbon atoms;
  (v) phenyl;
  (vi) substituted phenyl

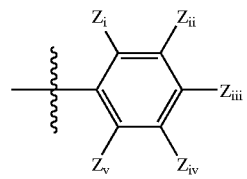

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;

(vii) a detectable label molecule; or (viii) a straight or branched chain alkenyl of 2 to 8 carbon atoms, inclusive;

wherein $Q_1$ is (C=O), $SO_2$ or (CN), provided when $Q_1$ is CN, then X is absent;

wherein one of $R_2$ and $R_3$ is a hydrogen atom and the other is (a) H;

(b) an alkyl of 1 to 8 carbon atoms, inclusive, which may be a straight chain or branched;

(c) a cycloalkyl of 3 to 6 carbon atoms, inclusive;

(d) an alkenyl of 2 to 8 carbon atoms, inclusive, which may be straight chain or branched; or (e) $R_aQ_2R_b$ wherein $Q_2$ is —O— or —S—; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is (a) H;

(b) an alkyl of 1 to 6 carbon atoms, inclusive, which may be a straight chain or branched;

wherein $R_5$ is

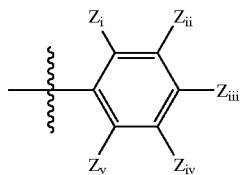

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is (a) H;

(b) an alkyl from 1 to 4 carbon atoms, inclusive, straight chain or branched;

wherein T is O or S, and pharmaceutically acceptable salts thereof, excluding 16-phenoxy-$LXA_4$ and 15-epi-16-(para-fluoro)-phenoxy-$LXA_4$.

3. A compound having the formula

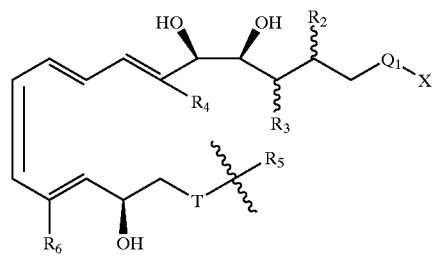

wherein X is $R_1$, $OR_1$, or $SR_1$;

wherein $R_1$ is (i) a hydrogen atom;

(ii) an alkyl of 1 to 8 carbons atoms, inclusive, which may be straight chain or branched;

(iii) a cycloalkyl of 3 to 10 carbon atoms;

(iv) an aralkyl of 7 to 12 carbon atoms;

(v) phenyl;

(vi) substituted phenyl

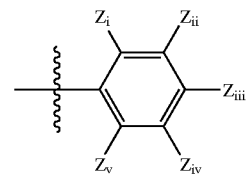

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;

(vii) a detectable label molecule; or (viii) a straight or branched chain alkenyl of 2 to 8 carbon atoms, inclusive;

wherein $Q_1$ is (C=O), $SO_2$ or (CN), provided when $Q_1$ is CN, then X is absent;

wherein one of $R_2$ and $R_3$ is a hydrogen atom and the other is (a) H;

(b) an alkyl of 1 to 8 carbon atoms, inclusive, which may be a straight chain or branched;

(c) a cycloalkyl of 3 to 6 carbon atoms, inclusive;

(d) an alkenyl of 2 to 8 carbon atoms, inclusive, which may be straight chain or branched; or (e) $R_aQ_2R_b$ wherein $Q_2$ is —O— or —S—; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is (a) H;

(b) an alkyl of 1 to 6 carbon atoms, inclusive, which may be a straight chain or branched;

wherein $R_5$ is

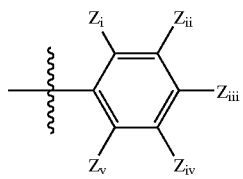

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;

wherein $R_6$ is
(a) H;
(b) an alkyl from 1 to 4 carbon atoms, inclusive, straight chain or branched;

wherein T is O or S, and pharmaceutically acceptable salts thereof, excluding 16-phenoxy-LXA$_4$ and 15-epi-16-(para-fluoro)-phenoxy-LXA$_4$.

4. A compound having the formula:

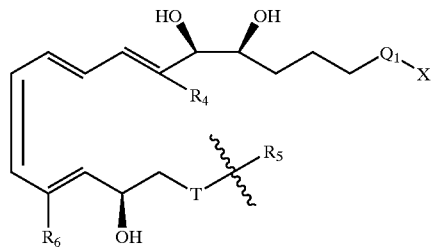

wherein X is $R_1$, $OR_1$, or $SR_1$;
wherein $R_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

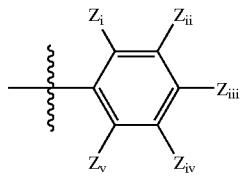

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is $(C=O)$, $SO_2$ or $(CN)$, provided when $Q_1$ is CN, then X is absent;

wherein $R_4$ is
(a) H;
(b) an alkyl of 1 to 6 carbon atoms, inclusive, which may be a straight chain or branched;

wherein $R_5$ is

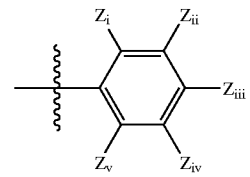

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;

wherein $R_6$ is
(a) H;
(b) an alkyl from 1 to 4 carbon atoms, inclusive, straight chain or branched;

wherein T is O or S, and pharmaceutically acceptable salts thereof, excluding 16-phenoxy-LXA$_4$ and 15-epi-16-(para-fluoro)-phenoxy-LXA$_4$.

5. A pharmaceutical composition comprising a compound having the formula

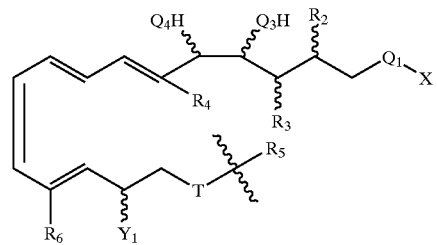

wherein X is $R_1$, $OR_1$, or $SR_1$;
wherein $R_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

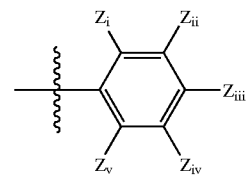

wherein $Z_i$, $Z_{ii}$, $Z_{iii}$, $Z_{iv}$ and $Z_v$ are each independently selected from $-NO_2$, $-CN$, $-C(=O)-$ $R_1$, —$SO_3H$, a hydrogen atom, halogen, methyl, —$OR_x$, wherein $R_x$ is 1 to 8 carbon atoms, inclusive, which may be a straight chain or branched, and hydroxyl;

(vii) a detectable label molecule; or (viii) a straight or branched chain alkenyl of 2 to 8 carbon atoms, inclusive;

wherein $Q_1$ is (C=O), $SO_2$ or (CN), provided when $Q_1$ is CN, then X is absent;

wherein $Q_3$ and $Q_4$ are each independently O, S or NH;

wherein one of $R_2$ and $R_3$ is a hydrogen atom and the other is (a) H;

(b) an alkyl of 1 to 8 carbon atoms, inclusive, which may be a straight chain or branched;

(c) a cycloalkyl of 3 to 6 carbon atoms, inclusive;

(d) an alkenyl of 2 to 8 carbon atoms, inclusive, which may be straight chain or branched; or (e) $R_aQ_2R_b$ wherein $Q_2$ is —O— or —S—; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is (a) H;

(b) an alkyl of 1 to 6 carbon atoms, inclusive, which may be a straight chain or branched;

wherein $R_5$ is

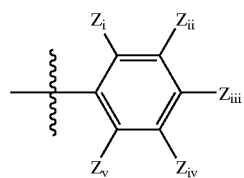

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is (a) H;

(b) an alkyl from 1 to 4 carbon atoms, inclusive, straight chain or branched;

wherein T is O or S, and pharmaceutically acceptable salts thereof; and a pharmaceutically acceptable carrier, provided 16-phenoxy-$LXA_4$ is excluded and provided when said compound is 15-epi-16-(para-fluoro)-phenoxy-$LXA_4$, said pharmaceutically acceptable carrier is not a ketone.

6. The pharmaceutical composition of claim 5, wherein said ketone is not acetone.

* * * * *